US009271667B2

(12) United States Patent
Robbins et al.

(10) Patent No.: US 9,271,667 B2
(45) Date of Patent: Mar. 1, 2016

(54) LANCING DEVICE WITH INDEPENDENT DRIVE CORE

(75) Inventors: Avi M. Robbins, Atlanta, GA (US); David R. Buenger, Roswell, GA (US)

(73) Assignee: FACET TECHNOLOGIES, LLC, Atlanta, GA (US)

(*) Notice: Subject to any disclaimer, the term of this patent is extended or adjusted under 35 U.S.C. 154(b) by 0 days.

(21) Appl. No.: 13/589,546

(22) Filed: Aug. 20, 2012

(65) Prior Publication Data

US 2012/0316592 A1 Dec. 13, 2012

Related U.S. Application Data

(63) Continuation of application No. 12/298,194, filed as application No. PCT/US2007/067411 on Apr. 25, 2007, now Pat. No. 8,267,950.

(60) Provisional application No. 60/794,809, filed on Apr. 25, 2006, provisional application No. 60/804,877, filed on Jun. 15, 2006.

(51) Int. Cl.
*A61B 5/151* (2006.01)
*A61B 5/15* (2006.01)

(52) U.S. Cl.
CPC ........... *A61B 5/1411* (2013.01); *A61B 5/15186* (2013.01); *A61B 2560/0443* (2013.01); *Y10T 29/49826* (2015.01)

(58) Field of Classification Search
CPC ............. A61B 5/1411; A61B 5/15186; A61B 2560/0443; Y10T 29/49826
USPC .................. 606/181–185, 117; 600/573, 583; 604/131, 134
See application file for complete search history.

(56) References Cited

U.S. PATENT DOCUMENTS

| | | | |
|---|---|---|---|
| 4,976,724 A | 12/1990 | Nieto et al. |
| 5,342,382 A | 8/1994 | Brinkerhoff et al. |
| 5,613,978 A | 3/1997 | Harding |
| 5,730,753 A | 3/1998 | Morita |
| 5,984,940 A | 11/1999 | Davis et al. |
| 6,022,366 A | 2/2000 | Schraga |
| 6,045,567 A | 4/2000 | Taylor et al. |
| D428,150 S | 7/2000 | Ruf et al. |
| 6,156,051 A | 12/2000 | Schraga |

(Continued)

FOREIGN PATENT DOCUMENTS

| | | |
|---|---|---|
| EP | 1535573 A2 | 1/2005 |
| WO | 2006118224 A1 | 9/2006 |
| WO | 2006138634 A2 | 12/2006 |

OTHER PUBLICATIONS

International Search Report for PCT/US2007/067411; Feb. 20, 2008; 1 pg.

*Primary Examiner* — Ryan Severson
*Assistant Examiner* — Rachel S Papeika
(74) *Attorney, Agent, or Firm* — Gardner Groff Greenwald & Villanueva, PC

(57) ABSTRACT

A medical lancing device including an independent drive core mechanism incorporating all or a substantial portion of the functional components of the lancing device, whereby the independent drive core mechanism can be incorporated into multiple different external housing configurations for more efficient design and manufacture. Axial adjustment of the position of the independent drive core mechanism within the housing provides lancing penetration depth control.

13 Claims, 36 Drawing Sheets

(56) References Cited

U.S. PATENT DOCUMENTS

| | | |
|---|---|---|
| 6,197,040 B1 | 3/2001 | LeVaughn et al. |
| 6,530,937 B1 | 3/2003 | Schraga |
| 6,613,064 B2 | 9/2003 | Rutynowski et al. |
| 6,645,219 B2 | 11/2003 | Roe |
| 6,706,159 B2 | 3/2004 | Moerman et al. |
| 6,793,633 B2 | 9/2004 | Douglas et al. |
| 6,811,557 B2 | 11/2004 | Schraga |
| 6,852,119 B1 | 2/2005 | Abulhaj et al. |
| 6,887,253 B2 | 5/2005 | Schraga |
| 7,077,828 B2 | 7/2006 | Kuhr et al. |
| 7,105,006 B2 | 9/2006 | Shraga |
| 7,175,641 B1 | 2/2007 | Schraga |
| 7,175,643 B2 | 2/2007 | Shi |
| 7,211,052 B2 | 5/2007 | Roe |
| 7,288,102 B2 | 10/2007 | Griffin et al. |
| 7,297,152 B2 | 11/2007 | Fukuzawa et al. |
| 7,311,718 B2 | 12/2007 | Schraga |
| 7,322,997 B2 | 1/2008 | Shi |
| D562,981 S | 2/2008 | Trissel et al. |
| 7,329,227 B2 | 2/2008 | Schramm |
| 7,452,366 B2 | 11/2008 | Chen et al. |
| 7,470,238 B2 | 12/2008 | Sakata et al. |
| 7,481,818 B2 | 1/2009 | Allen et al. |
| 7,621,931 B2 | 11/2009 | Shraga |
| 7,651,512 B2 | 1/2010 | Chelak et al. |
| 7,867,244 B2 | 1/2011 | Lathrop et al. |
| 7,901,363 B2 | 3/2011 | Duchon et al. |
| 7,905,898 B2 | 3/2011 | Schraga |
| 7,909,842 B2 | 3/2011 | Flynn et al. |
| 7,914,547 B2 | 3/2011 | Curry et al. |
| 7,955,348 B2 | 6/2011 | Trissel et al. |
| 8,016,848 B2 | 9/2011 | Lathrop et al. |
| 8,048,097 B2 | 11/2011 | Schraga |
| 8,118,825 B2 | 2/2012 | Schraga |
| 8,257,380 B2 | 9/2012 | Schraga |
| 2003/0088261 A1 | 5/2003 | Schraga |
| 2003/0187470 A1* | 10/2003 | Chelak et al. ............... 606/182 |
| 2004/0186500 A1 | 9/2004 | Koike et al. |
| 2004/0249405 A1 | 12/2004 | Watanabe et al. |
| 2005/0004494 A1 | 1/2005 | Perez et al. |
| 2005/0125019 A1 | 6/2005 | Kudrna et al. |
| 2005/0159768 A1 | 7/2005 | Boehm et al. |
| 2005/0234495 A1 | 10/2005 | Schraga |
| 2007/0055298 A1 | 3/2007 | Uehata et al. |

* cited by examiner

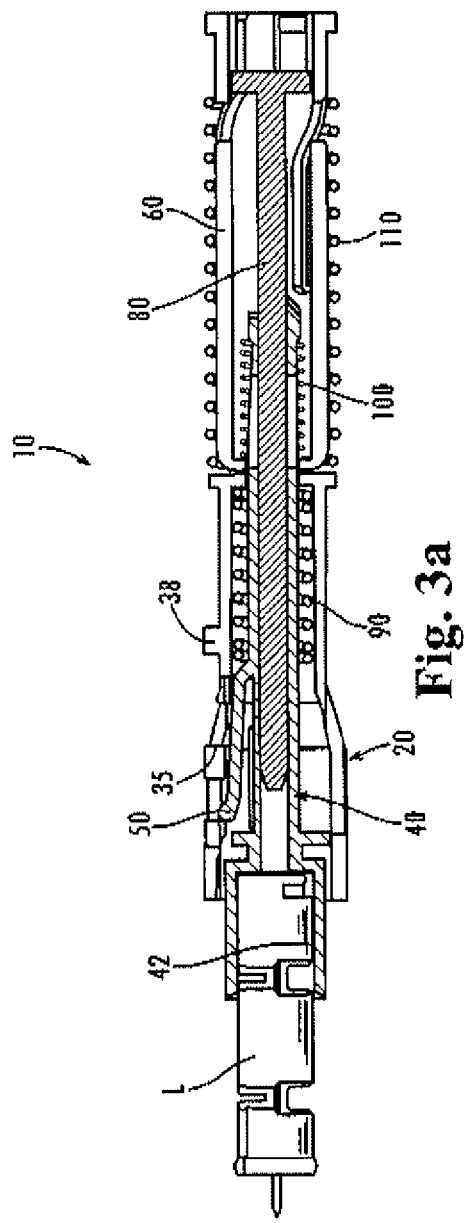

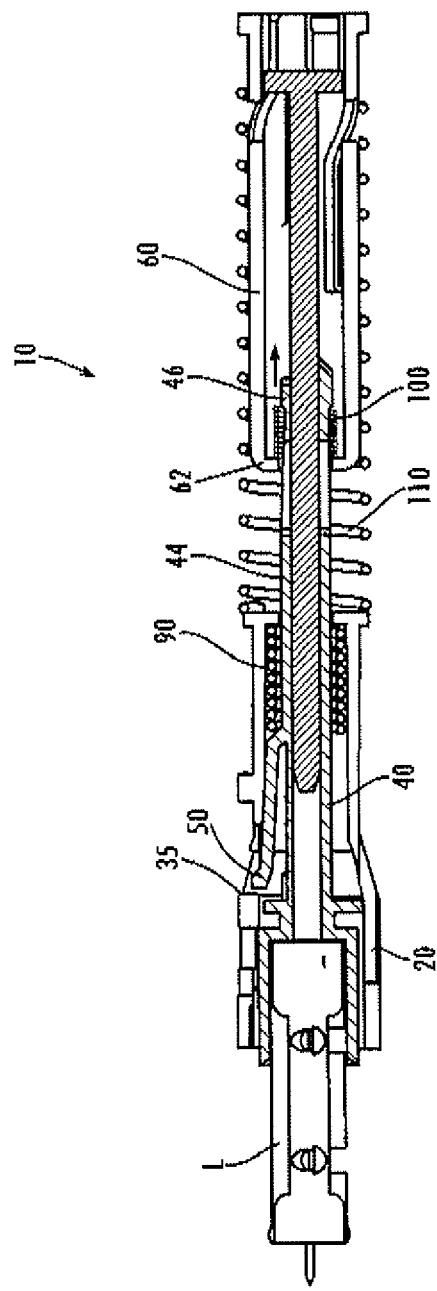

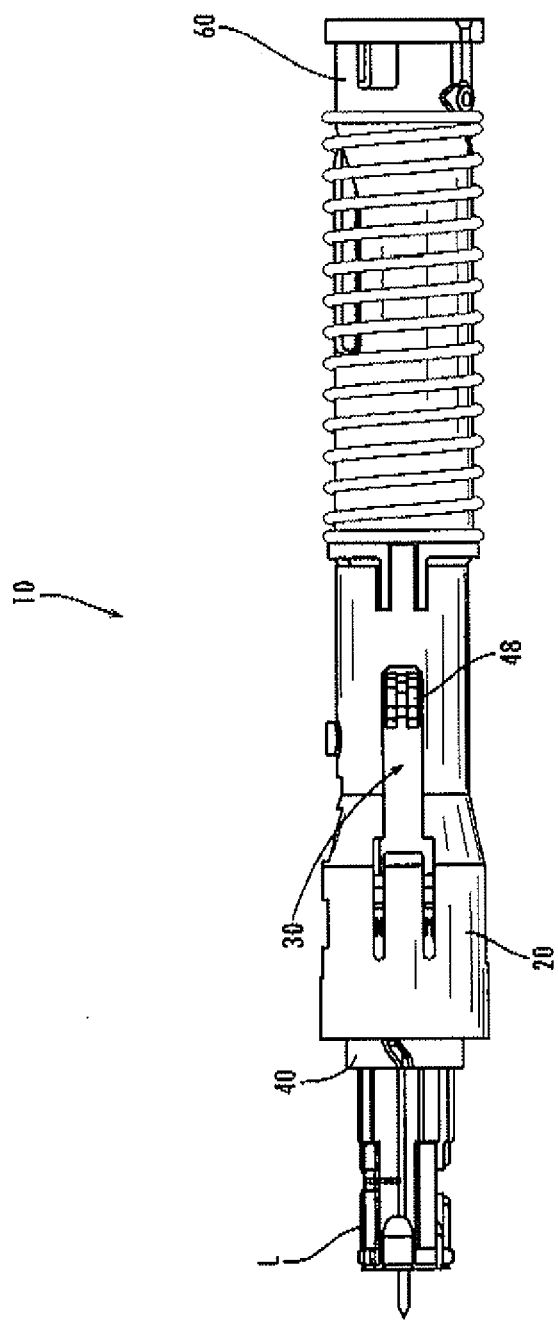

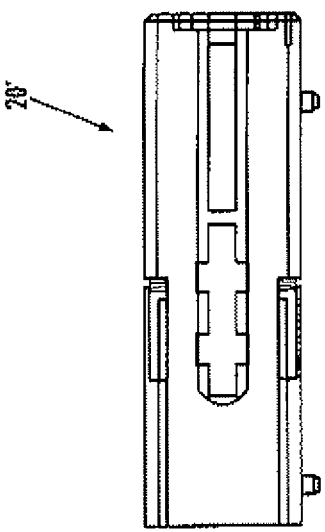
Fig. 15a
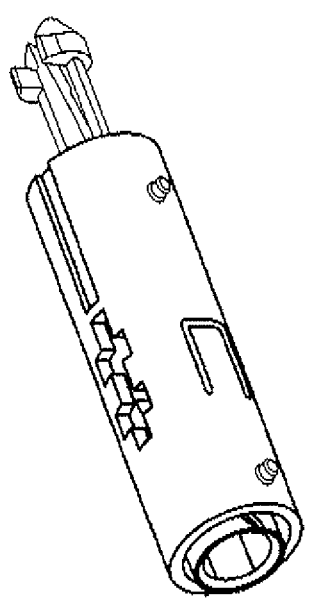
Fig. 14b
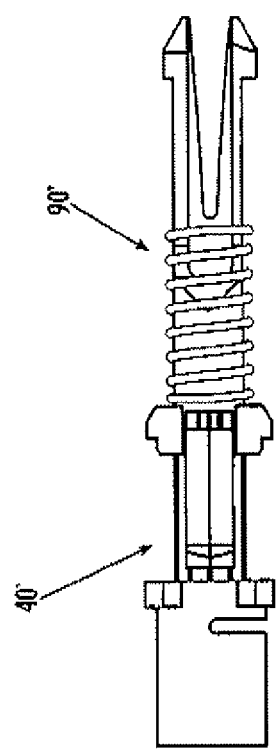

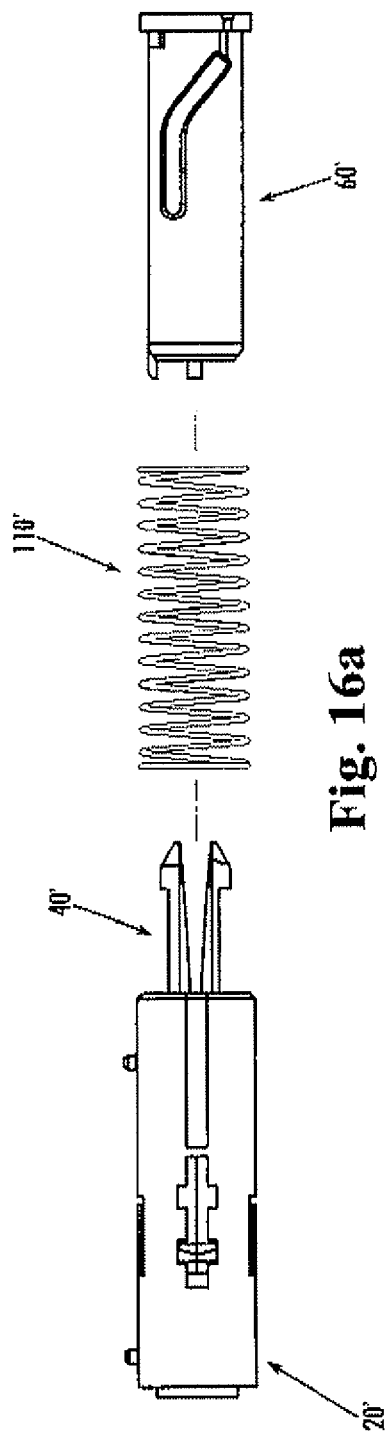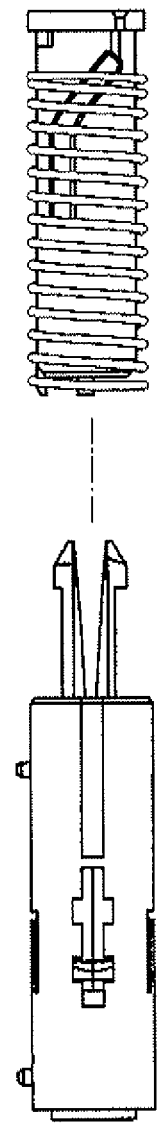

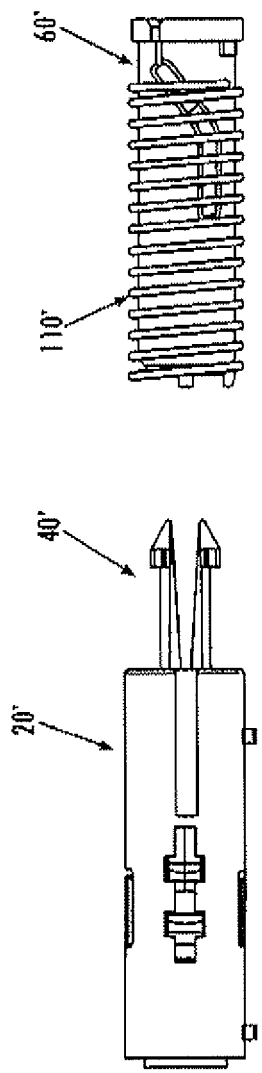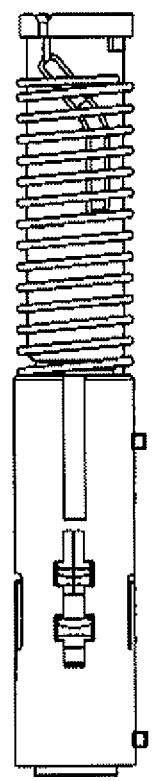
Fig. 17a
Fig. 17b

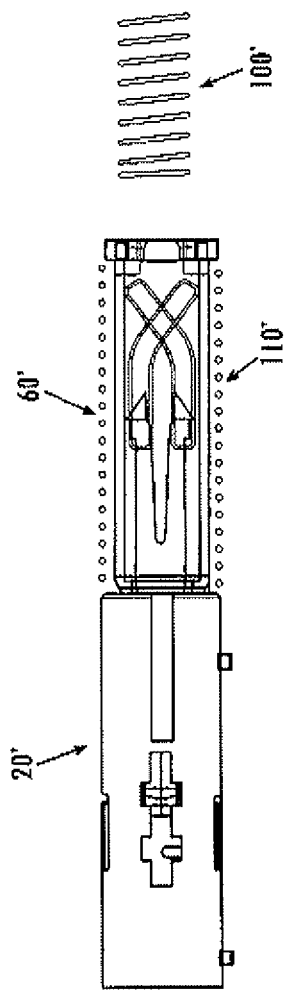
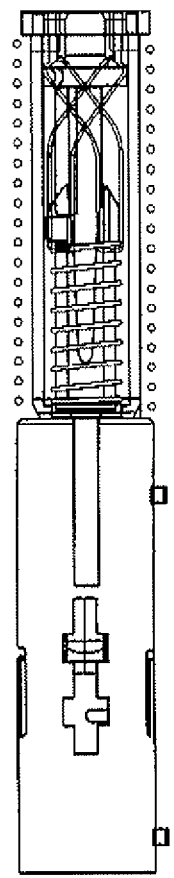
Fig. 19a
Fig. 19b

LANCING DEVICE WITH INDEPENDENT DRIVE CORE

CROSS-REFERENCE TO RELATED APPLICATIONS

This application is a continuation of U.S. Non-Provisional patent application Ser. No. 12/298,194 filed Oct. 23, 2008, which is a U.S. National Phase of PCT/US07/67411 filed Apr. 25, 2007, which claims the priority benefit of U.S. Provisional Patent Application Ser. No. 60/794,809 filed Apr. 25, 2006, and U.S. Provisional Patent Application Ser. No. 60/804,877 filed Jun. 15, 2006, all of which are hereby incorporated herein by reference in their entirety for all purposes.

TECHNICAL FIELD

The present invention relates generally to a lancing device for medical sampling of blood or other body fluids of a human or animal subject.

BACKGROUND OF THE INVENTION

Many medical procedures require puncturing of the skin, and sometimes underlying tissues, of a human or animal subject. For example, a sharp lancet tip is commonly used to prick the subject's skin at a lancing site to obtain a sample of blood or other body fluid, as for example in blood glucose monitoring by diabetics and in blood typing and screening applications.

In order to obtain an adequate sample size with minimal or no pain to the subject, it is often desirable to provide for adjustment of the depth of penetration of the lancet tip into the subject's skin. For example, individuals with thicker skin or deeper capillaries may require lancing to a deeper penetration depth than individuals having thinner skin or shallower capillaries. Also, alternate site lancing, for example on the forearm or other body portion of the subject, rather than fingertip sampling, may require a deeper penetration depth.

Common mechanisms for accomplishing depth adjustment include movable stop members for limiting the stroke of a lancet or lancet carrier, and adjustable endcaps for varying the position of the sampling site relative to the forward extent of the lancet stroke. Some known depth adjustment mechanisms for lancing devices may contribute to the transmission of an unacceptable degree of vibration to the lancing site, which may increase the perception of pain from the lancing procedure. Also, in many instances it may be desirable to provide a more precise adjustment of penetration depth than some known depth adjust mechanisms provide. Accordingly, it can be seen that continued improvement to depth control in lancing devices is desirable.

Additionally, in the design of lancing devices it is often desirable to provide a distinctive and unique product configuration to a lancing device, for purposes of product differentiation in the marketplace, for aesthetic and/or functional compatibility with related products such as blood glucose meters, and/or for branding purposes. For example, a first supplier may wish for their model of lancing device to have one shape, color scheme, etc., whereas a second supplier may wish for their model of lancing device to have a different shape, color scheme, etc. The expense and time involved in designing and developing a commercially acceptable lancing device can be considerable. Accordingly, it can be seen that improvements to lancing devices and to design, development and manufacturing methods for lancing devices that permit differentiation of products more efficiently and economically is desirable.

It is to the provision of improved lancing devices, and to improved design, development and manufacturing methods for lancing devices meeting this and other needs that the present invention is primarily directed.

SUMMARY OF THE INVENTION

In example embodiments, the lancing device of the present invention includes an independent drive core mechanism that is adaptable to use in connection with a variety of external housing configurations. Adjustment of the axial position of the independent drive core mechanism within the external housing allows precise depth adjustment in various forms of the invention that are easy and intuitive for a user to operate. Moving the independent drive core mechanism forward (toward the lancing site) in the external housing generally results in a deeper penetration, whereas moving the independent drive core mechanism rearward (away from the lancing site) in the external housing generally results in a shallower penetration.

Because the independent drive core mechanism of the present invention is relatively compact and includes all or a substantial portion of the functional components of the lancing device, it can be efficiently incorporated into different external housing configurations. The independent drive core mechanism thus provides a suitable off-the-shelf mechanism that a designer or manufacturer can utilize to streamline the design, development and production of lancing devices. In terms of product differentiation between lancing devices of different suppliers, it has been discovered that it may be immaterial to both the user and the supplier whether the internal mechanical workings of the lancing devices are the same or different, so long as the end user perceives the devices to be different from the outside. In such cases, it has been discovered that it will often be more efficient, both in terms of manufacturing cost and design lead-time, to utilize a common independent drive core mechanism according to the present invention, which is adaptable for use with different external housing configurations.

In example embodiments, the external housing of a lancing device according to the present invention includes one or more components for interfacing with the independent drive core mechanism so as to provide positional adjustment of the independent drive core mechanism within the external housing for depth control. In alternate embodiments, the independent drive core mechanism is fixed in position in the external housing, resulting in a single depth lancing device. In still other embodiments, the independent drive core mechanism is fixed in position in the external housing, and the external housing includes another form of depth control mechanism.

In one aspect, the invention is a lancing device, preferably including an external housing having a lancet opening, and an independent drive core mechanism positioned at least partially within the external housing. The independent drive core mechanism includes a mechanism housing; a drive plunger for receiving a lancet, the drive plunger being translationally mounted for advancement and retraction within the mechanism housing; a drive spring engaged between the mechanism housing and the drive plunger, for advancing the drive plunger toward the lancet opening; and a charging housing for retracting the drive plunger and energizing the drive spring.

In another aspect, the invention is an independent drive core mechanism for a lancing device. The independent drive core mechanism preferably includes a mechanism housing having a bore extending axially therethough; a drive plunger having a receiver for releasably engaging a lancet, the drive plunger being translationally mounted for advancement and retraction within the bore of the mechanism housing between an advanced position and a retracted position; a drive spring engaged between the mechanism housing and the drive plunger, for advancing the drive plunger toward the advanced position; a charging housing for retracting the drive plunger and energizing the drive spring; and at least one retention member for engagement with a cooperating portion of an external housing.

In still another aspect, the invention is a drive mechanism for installation within a lancing device housing. The drive mechanism preferably includes a mechanism housing, a drive plunger movable between an advanced position and a retracted position relative to the mechanism housing, wherein a constant stroke of travel is defined between the advanced position and the retracted position, and a drive spring engaged between the mechanism housing and the drive plunger to propel the drive plunger along the stroke of travel. Optionally, a depth-adjust mechanism varies the position of the constant stroke length drive mechanism within a lancing device housing to provide lancing penetration depth adjustment.

In another aspect, the invention is a method of designing lancing devices, the method preferably including specifying an independent drive core mechanism having a mechanism housing, a lancet carrier translationally mounted within the mechanism housing, a drive spring for advancing the lancet carrier, and a return spring for retracting the lancet carrier. The method preferably further includes specifying the design of a first lancing device incorporating the independent drive core mechanism into a first external housing configuration, and specifying the design of a second lancing device incorporating the independent drive core mechanism into a second external housing configuration different from the first external housing configuration.

In another aspect, the invention is a method of manufacturing lancing devices, the method preferably including providing an independent drive core mechanism having a mechanism housing, a lancet carrier translationally mounted within the mechanism housing, a drive spring for advancing the lancet carrier, and a return spring for retracting the lancet carrier. The method preferably further includes assembling a first lancing device by installation of the independent drive core mechanism into a first external housing configuration, and assembling a second lancing device by installation of the independent drive core mechanism into a second external housing configuration different from the first external housing configuration.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 3a is a cross-sectional side view of the mechanical drive core of FIG. 1, shown in a neutral state.

FIG. 4a is a cross-sectional side view of the mechanical drive core of FIG. 1, shown in a charging state.

FIG. 5b is a side view of the mechanical drive core of FIG. 1, shown in the charged state.

FIGS. 14a and 14b show a subsequent step of the assembly sequence.

FIGS. 15a, 15b and 15c show a subsequent step of the assembly sequence.

FIGS. 16a and 16b show a subsequent step of the assembly sequence.

FIGS. 17a and 17b show a subsequent step of the assembly sequence.

FIGS. 19a and 19b show a subsequent step of the assembly sequence.

DETAILED DESCRIPTION OF EXAMPLE EMBODIMENTS

Figure 1:
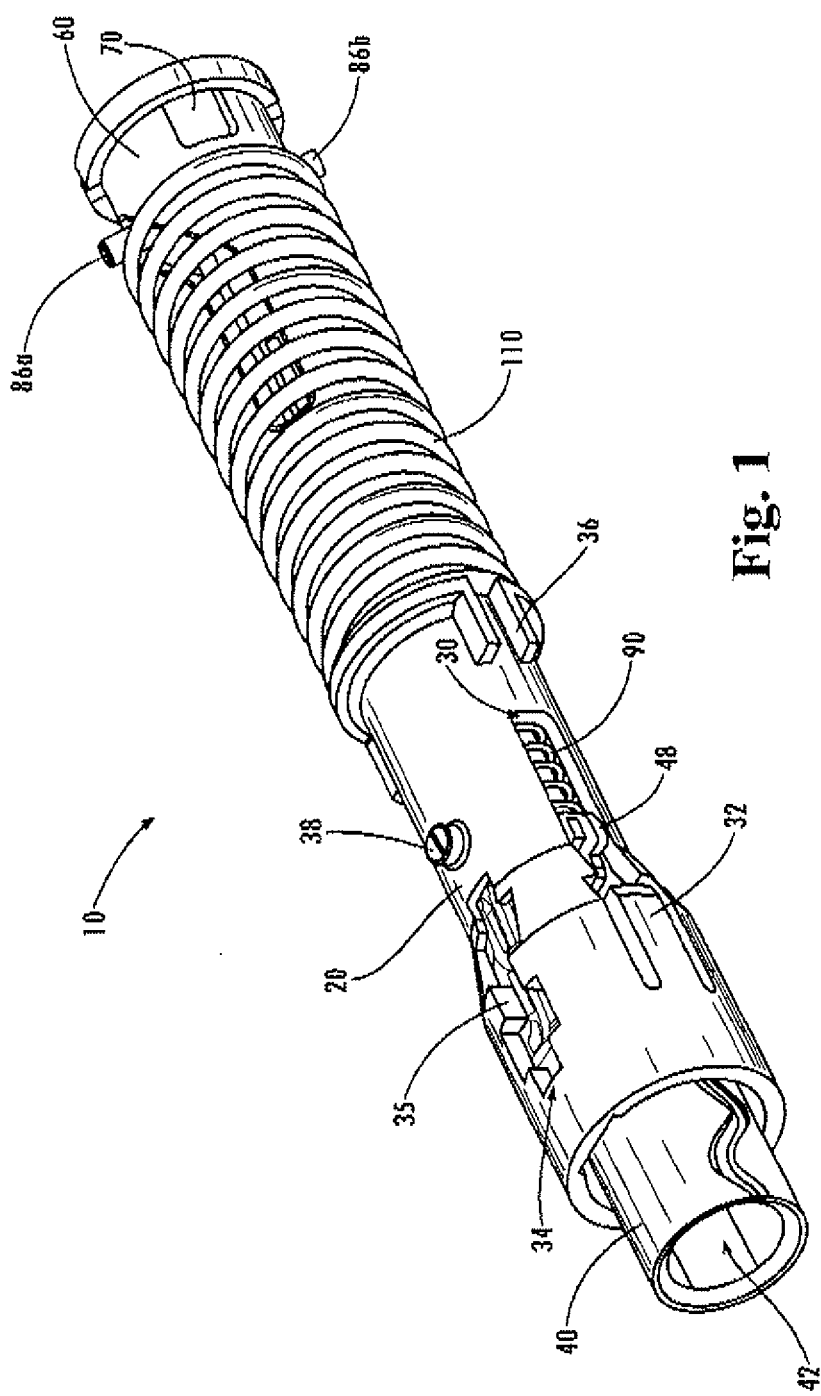
FIG. 1 is a perspective view of a mechanical drive core portion of a lancing device according to an example form of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference to FIGS. 1-9, an independent drive core mechanism 10 for a lancing device is shown according to an example form of the invention. The independent drive core mechanism 10 is preferably compact, and in the depicted embodiment has a generally cylindrical, narrow-profile, elongate outer geometry, for example having an aspect ratio (length:diameter) of at least 3:1. The independent drive core mechanism 10 generally comprises a mechanism housing 20 having a bore extending axially therethough; a drive plunger 40, a charging housing 60, and an ejector rod 80. A drive spring 90 is engaged between the mechanism housing 20 and the drive plunger 40, a return spring 100 is engaged between the drive plunger 40 and the charging housing 60, and an ejector spring 110 is engaged between the ejector rod 80 and the mechanism housing 20.

The mechanism housing 20 is a generally cylindrical sleeve having a wider proximal cylindrical section 22 at a first end, a narrower distal cylindrical section 24 at a second end thereof, and a tapering conical section 26 therebetween. An inwardly and outwardly projecting flange 28 extends from the second end of the mechanism housing 20, for engagement with a distal end of the drive spring 90 (on the forward face of the inwardly directed portion of flange 28), and with a proximal end of the ejector spring 110 (on the rear face of the outwardly directed portion of flange 28), when the independent drive core mechanism is assembled. The mechanism housing 20 is generally hollow, having an internal bore extending axially from the first end to the second end. A stroke-limiting slot 30 extends axially lengthwise through a lateral sidewall portion of the mechanism housing 20, along portions of the distal cylindrical section 24 and the conical section 26 thereof. A resiliently flexing finger 32 has a free end defining the proximal end of the stroke-limiting slot 30. The finger 32 flexes outwardly during assembly to allow installation of the drive plunger 40 into the mechanism housing 20. A trigger slot 34 extends axially lengthwise through an upper sidewall portion of the mechanism housing 20, along portions of the proximal cylindrical section 22, the distal cylindrical section 24, and the conical section 26 thereof. A shoulder or other catch member 35 projects into or adjacent the trigger slot 32. A channel or other guide member 36 extends axially along a lateral exterior sidewall of the mechanism housing 20, and an outwardly projecting member or lug 38 extends from an upper sidewall of the mechanism housing. The guide member 36 and/or the lug 38 serve as retention members for engagement with a cooperating portion of an external housing into which the independent drive core mechanism 10 is installed.

The drive plunger 40 is translationally mounted within the axially extending bore of the mechanism housing 20 for advancement and retraction between an advanced position and a retracted position. The drive plunger 40 includes a cup-shaped holder or receiver 42 at its proximal end for releasably engaging a lancet L of standard or customized configuration. The receiver 42 preferably retains the lancet with a friction fit, for example by means of a slotted cylindrical sidewall formed of resiliently flexible material, and having an internal dimension in its relaxed state of slightly less than the outer dimension of the lancet, such that the slotted sleeve flexes slightly and expands to frictionally receive the lancet upon insertion with light manual force. An axially elongate tube portion 44 of the drive plunger 40 extends distally from the receiver 42, and through an opening in the inwardly directed portion of the flange 28 at the distal end of the mechanism housing 20. The tube portion 44 of the drive plunger 40 defines an inner bore along its entire length, opening at its proximal end into the receiver, and also open at its distal free end. A tail portion 46 of the tube portion 44 of the drive plunger 40 has an expanded outer diameter or flared portion for engagement with a distal end of the return spring 100, which is coiled about the exterior of the tube portion of the drive plunger within the charging housing. The tail portion 46 is split along its length to permit the opposed side portions thereof to be flexed inwardly toward one another to receive the return spring 100 thereon and for assembly into the mechanism housing 20 and the charging housing 60. The drive spring 90 is coiled about the tube portion 44 of the drive plunger 40, within the mechanism housing 20. One or more laterally projecting wings 48 extend from an outer face of the drive plunger 40, and slide within the stroke-limiting slot 30 of the mechanism housing 20 to define the stroke of travel of the drive plunger relative to the mechanism housing. Contact between the wing(s) 48 against the finger 32 at the proximal end of the stroke-limiting slot 30 defines the advanced position of the drive plunger 40, and contact between the wing(s) against the distal end of the stroke-limiting slot defines the retracted position of the drive plunger. In this manner, a constant stroke distance of the drive plunger and the lancet carried therein is provided. Engagement of the wing(s) 48 within the stroke-limiting slot 30 also serves to prevent twisting of the drive plunger 40 relative to the mechanism housing 20. During assembly, the wings 48 cause the cantilevered finger 32 to flex outwardly as the drive plunger is installed into the mechanism housing, and the finger springs back after the wings have passed into the slot 30 to retain the drive plunger in place within the mechanism housing. A flexible trigger arm 50 extends in cantilevered fashion outwardly from the drive plunger 40, and is received in the trigger slot 34 of the mechanism housing 20. The free end of the trigger arm 50 releasably engages against the shoulder or catch member 35 of the trigger slot 34 of the mechanism housing 20 to retain the drive plunger 40 in its charged state until released by the user. The trigger arm 50 also engages a proximal end of the drive spring 90 as the drive plunger 40 is retracted during charging to compress and energize the drive spring. A guide flange or finger 52 extends from the drive plunger 40 for sliding engagement against an interior guide surface of the mechanism housing 20 to constrain the drive plunger to axial linear translational movement and substantially prevent lateral movement, thereby providing a smooth and linear path of travel to the lancet as it moves along its lancing stroke.

The charging housing 60 is a generally cylindrical, elongate tubular member having an inwardly directed flange 62 at its proximal end and an outwardly directed flange 64 at its distal end. The forward face of the inwardly directed flange 62 confronts the rear face of flange 28 of the mechanism housing, and the rear face of the inwardly directed flange 62 engages a proximal end of the return spring 100, when assembled. A diametrically opposed pair of slots 66a, 66b extends along the charging housing 60 from its distal end. As seen best with reference to FIGS. 8 and 9, distal portions of each of the slots 66a, 66b extend in a generally axial direction along the sidewalls of the charging housing 60, angularly slanted or helically curved medial portions of the slots extend proximally from the distal portions of the slots, and proximal portions of the slots extend generally axially forward from the angularly or helically oriented medial portions of the slots, whereby the distal and proximal portions of the slots are generally parallel but angularly offset by about 50° from one another. The distal portions of each of the slots 66a, 66b are relatively narrow, and the medial and proximal portions of the slots are relatively wide, such that pin retention pockets 68a, 68b are formed at the intersection of the distal and medial portions of the slots. The ejector spring 110 is coiled about the external surface of the charging housing 60. One or more channels 70a, 70b serve as rear retention members for engagement with an ejection interface or other cooperating portion of an external housing into which the drive core 10 is installed, to secure the drive core within the housing, maintain proper alignment during depth adjustment, and prevent the drive core from twisting relative to the housing.

The ejector rod 80 comprises an elongate cylindrical rod 82 having an outer diameter configured to slide smoothly within the inner bore of the tube portion 44 of the drive plunger 40, and a tapered proximal end. The ejector rod 80 further comprises a generally circular flange 84 at the distal end of the cylindrical rod 82, having a diameter configured to slide smoothly within the inside channel of the charging housing 60. A pair of diametrically opposed pins or fingers 86a, 86b extend outwardly from the flange 84, and are received within the slots 66a, 66b of the charging housing 60, such that when assembled the fingers 86a, 86b can freely slide within the slots between the retention pockets 68a, 68b and the proximal ends of the slots. Outer ends of the fingers 86a, 86b engage the distal end of the ejector spring 110. A stop or rib 88 extends laterally from a side face of the cylindrical rod 82 for abutment against a shelf or shoulder at the rear face of the tail portion 46 of the tube portion 44 of the drive plunger 40 to prevent inadvertent ejection of a lancet by advancement of the ejector rod 80 when the drive plunger is in its charged position (FIG. 8b).

Product Differentiation with Common Drive Core

FIGS. 10 and 11 show assembly of an independent drive core mechanism 10, as described above, into two different forms of lancing devices 200, 200' according to example embodiments of the invention. When it is stated herein that different forms of lancing devices incorporate a common independent drive core mechanism, it is not intended that the specific independent drive core mechanism unit be installed in each form of lancing device, but rather that different independent drive core mechanism units having a substantially common design may be installed in the different forms of lancing devices.

In the embodiment of FIG. 10, an independent drive core mechanism 10 is installed within a first form of external housing 202, whereas in the embodiment of FIG. 11, the same type of independent drive core mechanism 10 is installed within a second form of external housing 202' that is different from the first external housing. For example, the embodiment of FIG. 10 includes a first type of trigger release button 204, whereas the embodiment of FIG. 11 includes a different type of trigger release button 204'; and a knurled ring 206 is present on the embodiment of FIG. 11, but not on the embodiment of FIG. 10. In those embodiments of the lancing device of the present invention that provide lancing depth adjustment by means of varying the axial position of the drive core within the external housing, the trigger release button preferably includes or is coupled to an elongate fin that extends a sufficient axial span to contact the free end of the trigger arm 50 regardless of the position of the drive core within the housing. By sharing a common design of the independent drive core mechanism 10 between two or more different forms of lancing devices, product differentiation and different modes of product usage may be accomplished with improved efficiencies, as compared to previous methods of design, development and manufacture of lancing devices.

Because the internal workings of the lancing device are common to their shared independent drive core mechanisms, the independent drive core mechanism can be considered an off-the-shelf assembly, available for adaptation and use in a variety of different forms of lancing devices. Design, development and manufacturing costs and lead times may be reduced, because only the external housing and drive core mechanism interfaces (e.g., trigger-release interface, depth-adjust interface, charging interface, and/or ejection interface) will differ significantly between the different forms of lancing devices. Also, economies of scale may be improved by the provision of a common independent drive core mechanism adaptable for use in multiple forms of lancing devices.

For example, in the design of lancing devices, the present invention provides a method of designing lancing devices wherein a designer specifies a common independent drive core mechanism 10 such as that described above. The same or a different designer further specifies the design of a first lancing device incorporating the common independent drive core mechanism into a first external housing configuration. The same or a different designer further specifies the design of a second lancing device incorporating the common independent drive core mechanism into a second external housing configuration different from the first external housing configuration. The first and second lancing device designs are distinguishable in terms of their manner of operation and/or their external appearance or configuration, despite sharing a substantially common internal drive core mechanism.

In the manufacture of lancing devices, the present invention provides a manufacturing method wherein a common independent drive core mechanism such as that described above is assembled into a first lancing device by installation of the independent drive core mechanism into a first external housing configuration. The same or a different manufacturer assembles a second lancing device by installation of the common independent drive core mechanism into a second external housing configuration different from the first external housing configuration. The first and second lancing devices are distinguishable in terms of their manner of operation and/or their external appearance or configuration, despite sharing a substantially common internal drive core mechanism.

Depth Adjustment

The independent drive core mechanism 10 is optionally mounted within the external housing 202, 202' in an axially adjustable manner, whereby the user may selectively control the lancing depth by varying the axial position of the independent drive core mechanism forward (proximally) or back (distally) within the external housing. In its various forms, the interior structure of the external housing preferably includes one or more guidance surfaces for interfacing with cooperating guidance portions of the independent drive core mechanism, to restrict transverse movement and provide smooth axial movement of the independent drive core mechanism within the housing.

Figure 10A:
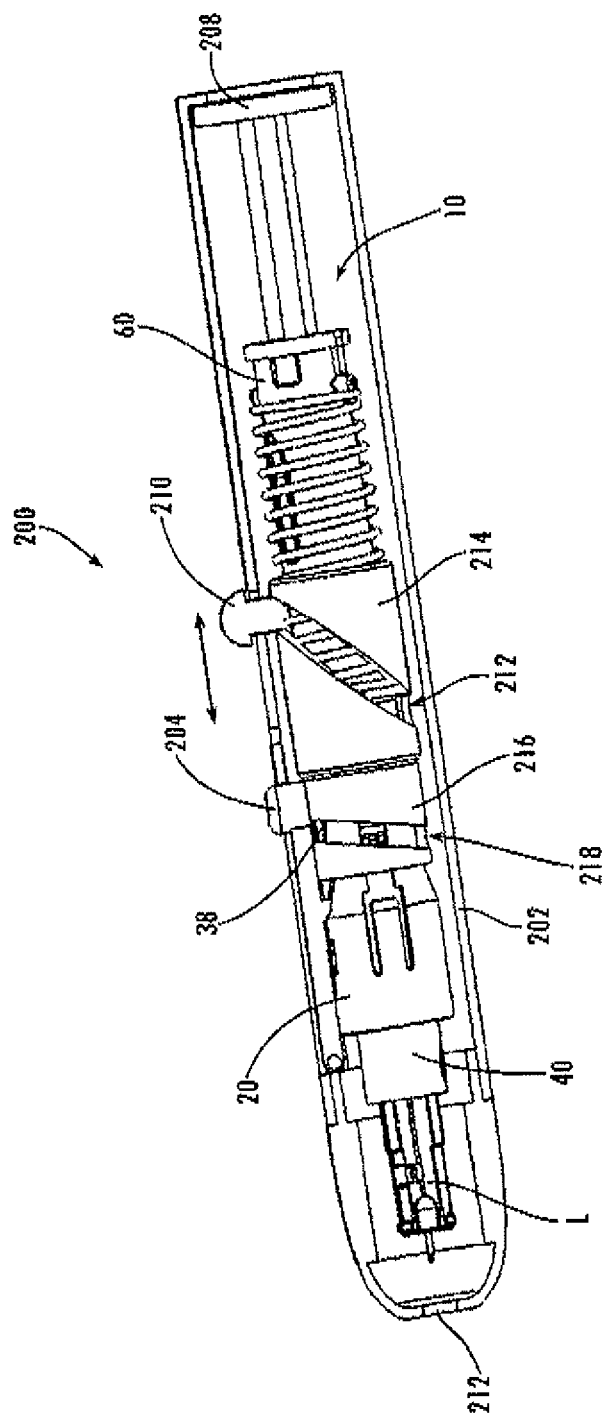
FIGS. 10a, 10b and 10c show a sequence of depth-adjustment positions of the mechanical drive core within a lancing device having a first type of outer housing.
Figure 10B:
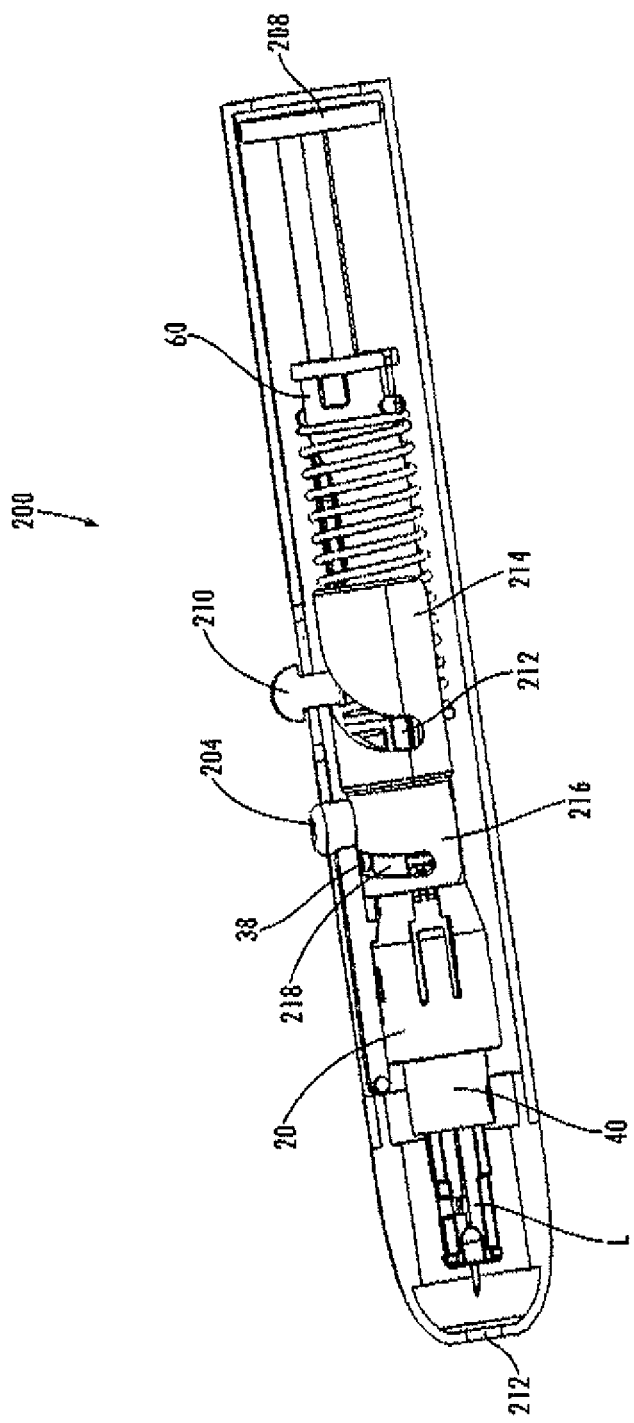
Figure 10C:
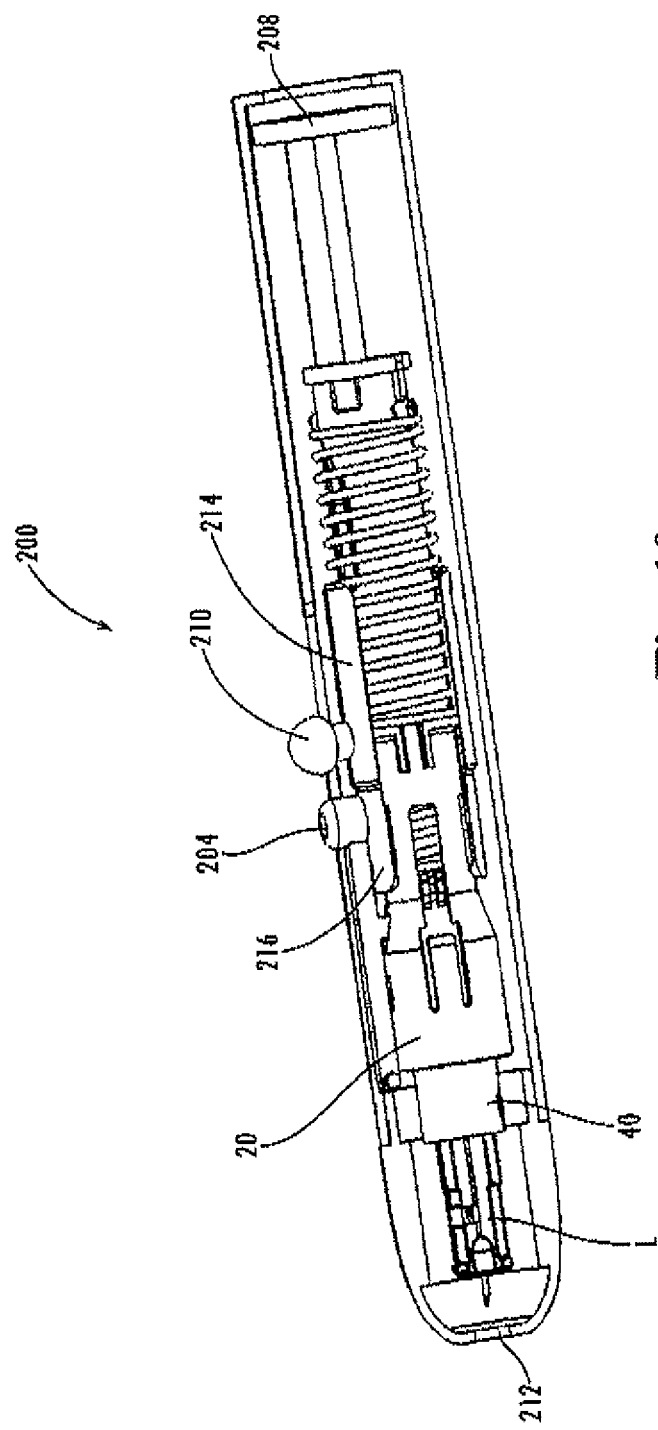

For example, in the embodiment of FIGS. 10a, 10b and 10c, a linearly actuated actuator 210 is moved axially forward and back to vary the position of the independent drive core mechanism forward and back within the external housing 202, between a shallow penetration depth setting (FIG. 10a), a medium penetration depth setting (FIG. 10b), and a deep penetration depth setting (FIG. 10c). Multiple discrete indexed depth settings can be provided, or the depth adjustment can be continuously variable between the shallow and deep settings. Indicia can be provided on the housing to specify the depth setting. Moving the independent drive core mechanism forward within the external housing 202 (toward the proximal end of the housing containing the lancet opening 212) results in a deeper lancing penetration, whereas moving the independent drive core mechanism rearward within the housing results in a shallower lancing penetration. The linearly actuated actuator 210 is preferably slidably coupled within an inclined or arcuate slot 212 in a depth-adjust linkage 214, which is in turn linked to a depth-adjust collar 216 having a slot 218, which engages the lug 38 on the mechanism housing 20 of the independent drive core mechanism 10. The slot 218 of the depth-adjust collar 216 preferably has a relatively smaller pitch or angle of inclination than the slot 212 of the depth-adjust linkage 214, such that a larger adjustment of the position of the actuator 210 results in a finer degree of adjustment of the penetration depth, thereby providing more precise depth adjustment.

Figure 11A:
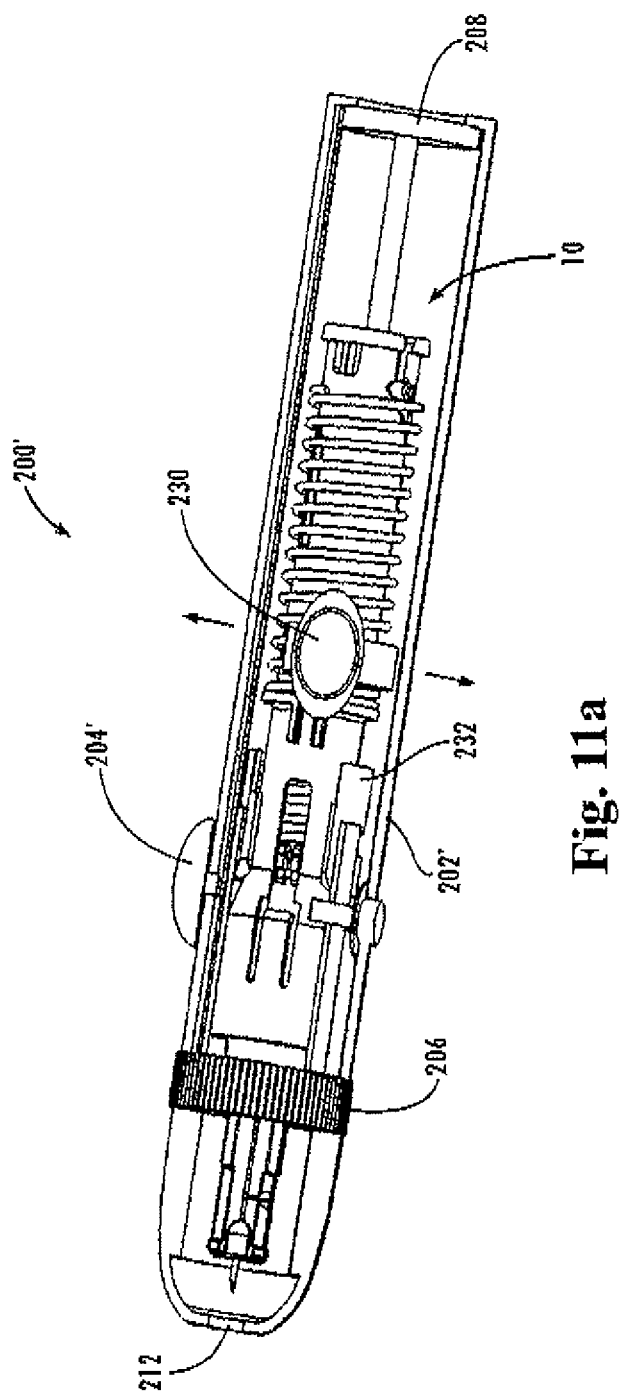
FIGS. 11a, 11b and 11c show a sequence of depth-adjustment positions of the mechanical drive core within a lancing device having a second type of outer housing.
Figure 11B:
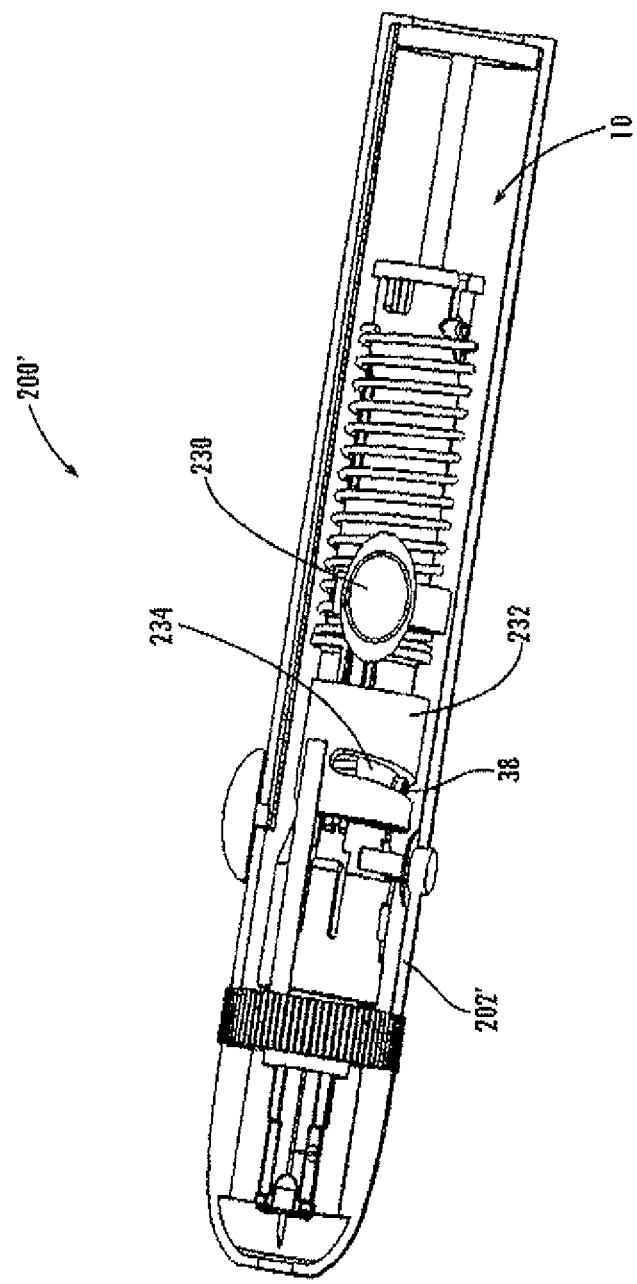
Figure 11C:
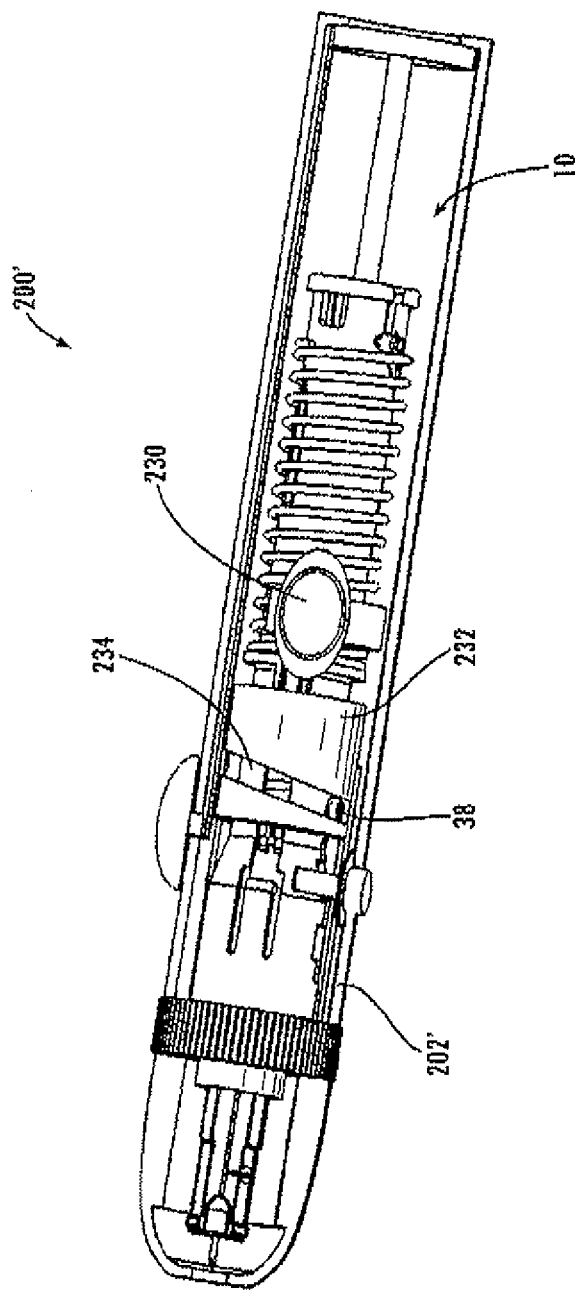
Figure 12:
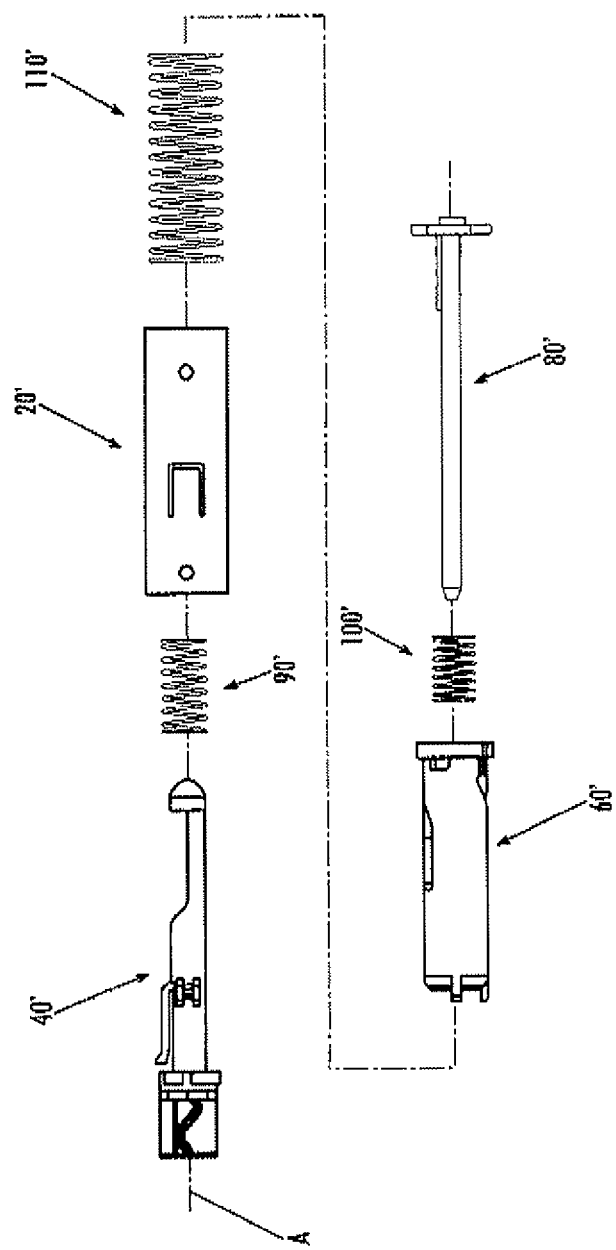
FIG. 12 is an assembly view showing the single-axis assembly of a drive core mechanism according to another embodiment of the invention.

In the embodiment of FIGS. 11a, 11b and 11c, a rotary actuated actuator 230 is moved circumferentially side to side to vary the position of the independent drive core mechanism 10 forward and back within the external housing 202', in a manner similar to that described above, between a shallow penetration depth setting (FIG. 11a), a medium penetration depth setting (FIG. 11b), and a deep penetration depth setting (FIG. 11c). The actuator extends through the shell of the external housing, and is linked to a depth-adjust collar 232 having a slot 234, which engages the lug 38 on the mechanism housing 20 of the independent drive core mechanism 10 to adjust the axial positioning of the independent drive core mechanism within the external housing.

Assembly of the Independent Drive Core Mechanism

FIGS. 12-20 show a sequence of assembly of a substantially similar drive core mechanism 10' according to an example form of the invention. As seen best with reference to FIG. 12, the components of the drive core are assembled linearly along a single axis A. Simplicity of manufacturing is further enhanced by a mechanism design incorporating only four molded components (typically plastic components), and three springs (typically metal coil springs), and requiring minimal or no manipulation of unconstrained springs under compression during assembly.

Figure 13A:
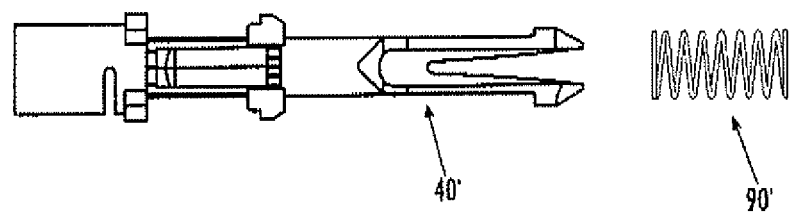
FIGS. 13a and 13b show a step of the assembly sequence of the drive core mechanism of FIG. 12, according to an example form of the invention.
Figure 13B:
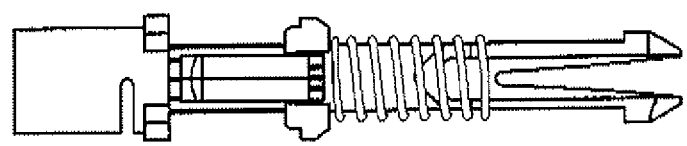

FIGS. 13a and 13b show installation of the drive spring 90' onto the drive plunger 40'. The slotted tail end of the drive plunger flexes inwardly to receive the drive spring, and then expands to retain the drive spring thereon. Inclined distal faces of the tail end of the drive plunger are optionally provided for ease of assembly of the drive spring onto the drive plunger.

Figure 14A:
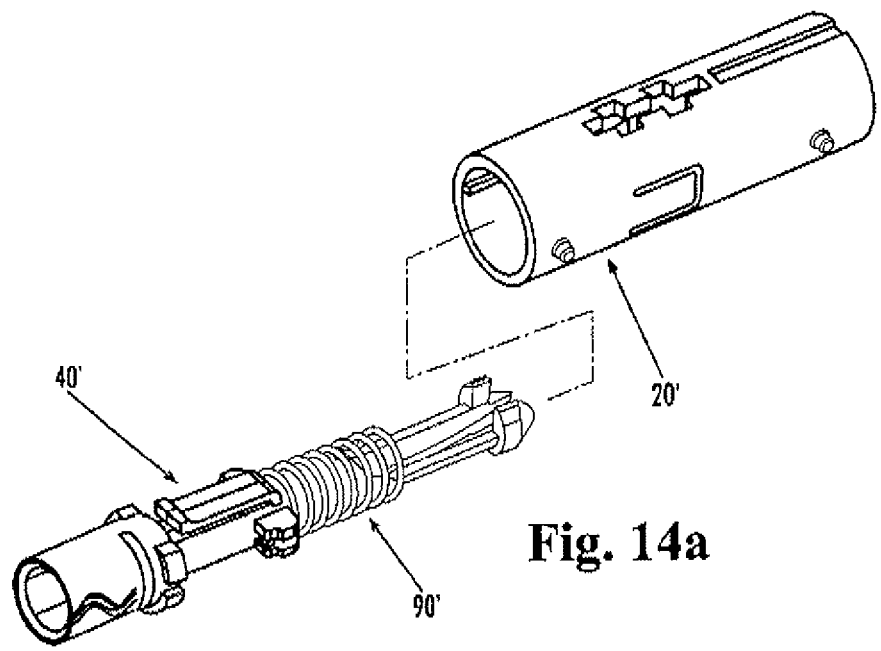
Figure 15B:
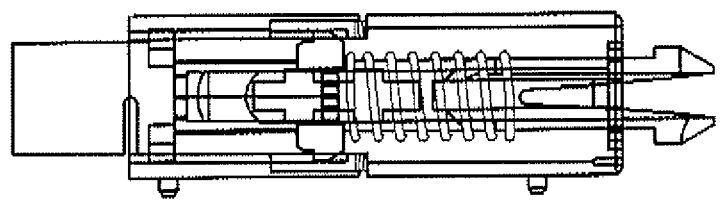
Figure 15C:
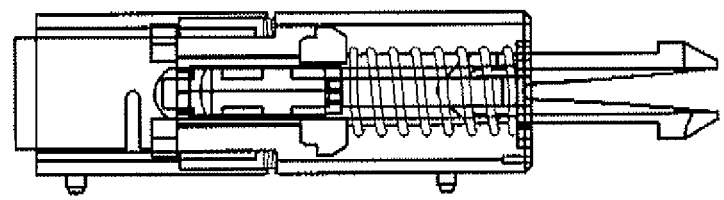

The assembled drive plunger 40' and drive spring 90' are then inserted axially into the mechanism housing 20', as shown in FIGS. 14 and 15. The laterally projecting wings of the drive plunger cause the resilient fingers of the mechanism housing to flex outwardly, and then snap back to retain the drive plunger within the mechanism housing. The slotted tail end of the drive plunger flexes inwardly again to fit through the distal end of the mechanism housing, causing the drive spring to act between the inside face of the distal end of the mechanism housing and the "wings" on the drive plunger.

The ejection spring 110' is then installed onto the outside of the charging housing 60', as shown in FIGS. 16a and 16b. The distal flange of the charging housing retains the ejection spring in place on the charging housing. The assembly of the charging housing 60' and ejection spring 110' is then placed over the tail end of the drive plunger 40', as shown in FIGS. 17a and 17b, with the opposed sides of the split tail of the drive plunger flexing inward to allow entry through a hole in the proximal flange of the charging housing, and then snapping back to prevent removal.

Figure 18:
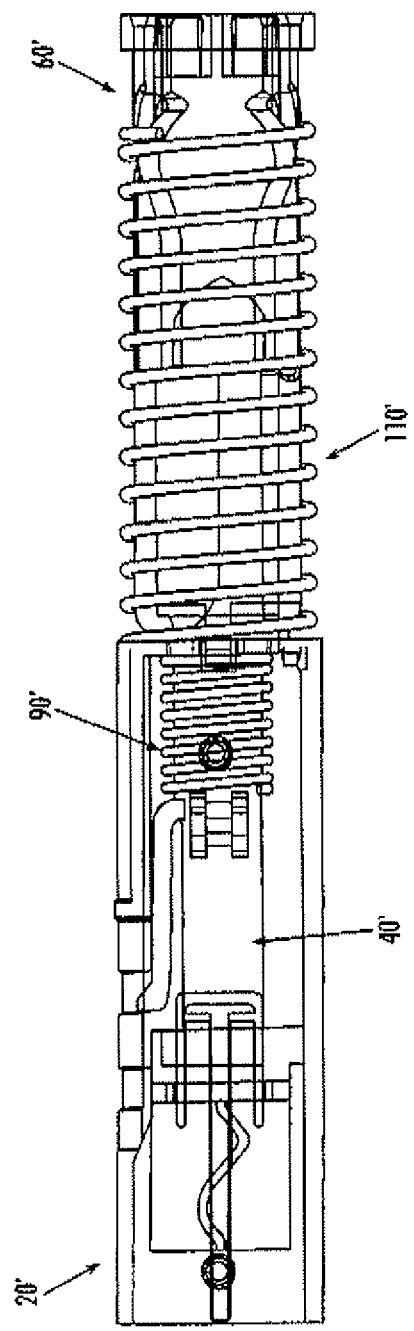
FIG. 18 shows a subsequent step of the assembly sequence.

The drive plunger 40' is retracted within the mechanism housing 20', into its charged configuration, with the drive spring 90' compressed and energized, and the trigger arm of the drive plunger engaged, as shown in FIG. 18. The return spring 100' is then inserted into the distal end of the charging housing 60' as shown in FIG. 19a, and onto the tail end of the drive plunger 40' as shown in FIG. 19b. Engagement of the return spring 100' between the flared portion of the drive plunger tail and the inward proximal flange of the charging housing couples the charging housing to the drive plunger and mechanism housing assembly.

Figure 20A:
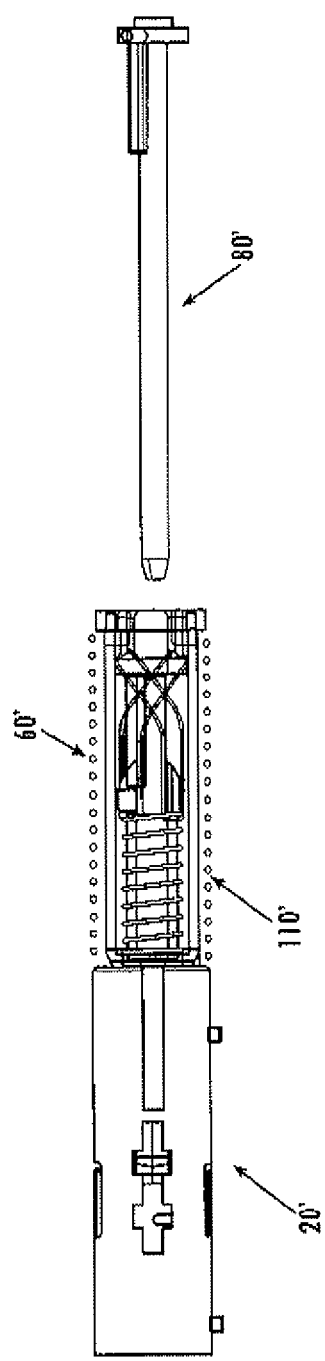
FIGS. 20a, 20b and 20c show a subsequent step of the assembly sequence.
Figure 20B:
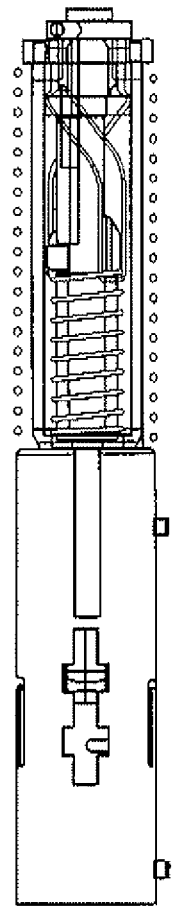
Figure 20C:
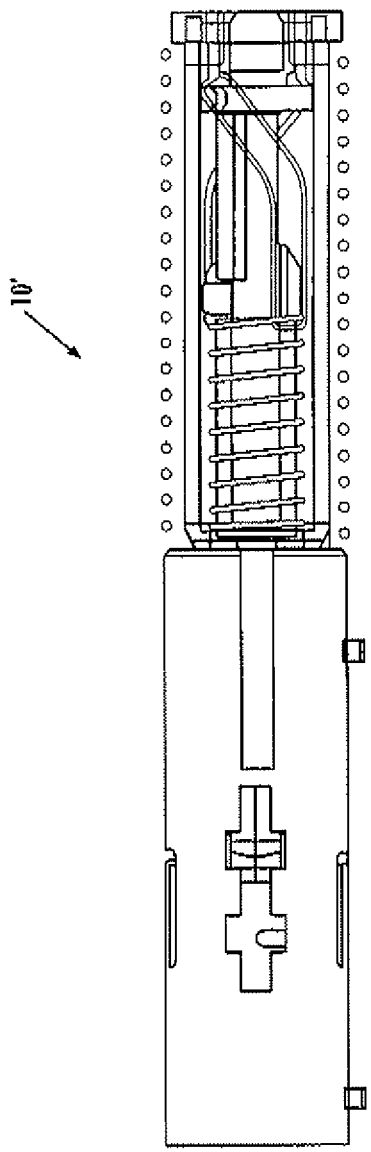

The ejector rod 80' is then inserted into the distal end of the charging housing, as shown in FIGS. 20a-20c. The pins of the ejector rod are preferably thicker than the distal portions of the slots of the charging housing, such that installation of the ejector rod flexes the slots apart to receive the pins, and the charging housing snaps back as the pins enter the pin retention pockets or the wider medial portions of the slots, to retain the ejector rod within the charging housing.

Use of the Lancing Device

Figure 2A:
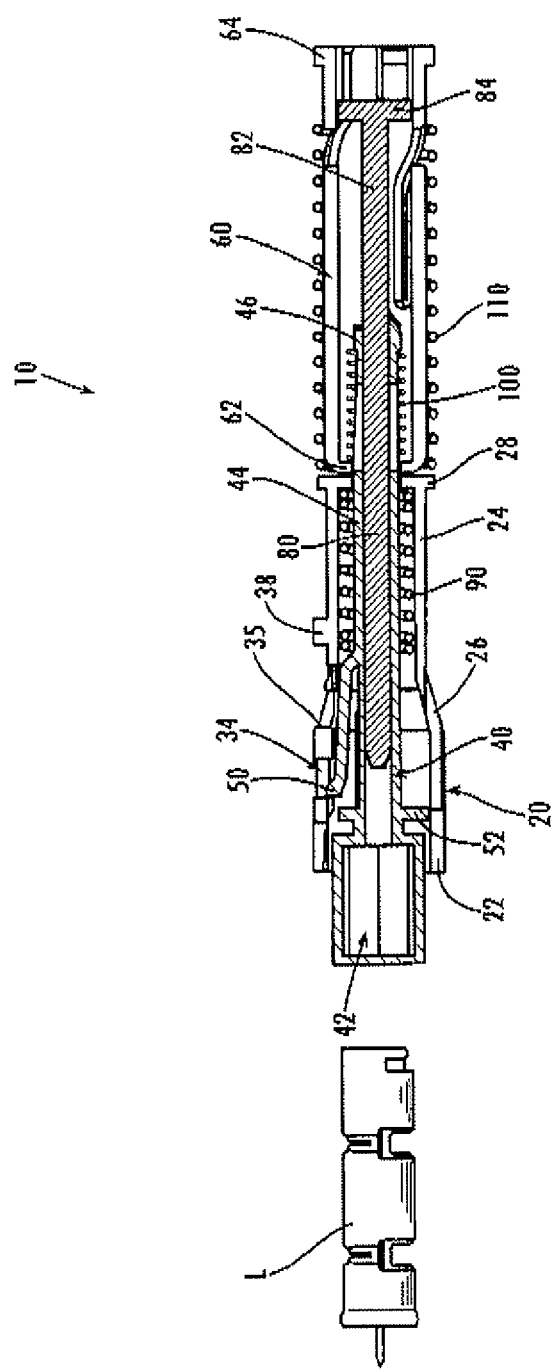
FIG. 2a is a cross-sectional side view of the mechanical drive core of FIG. 1, shown in a loading state.
Figure 2B:
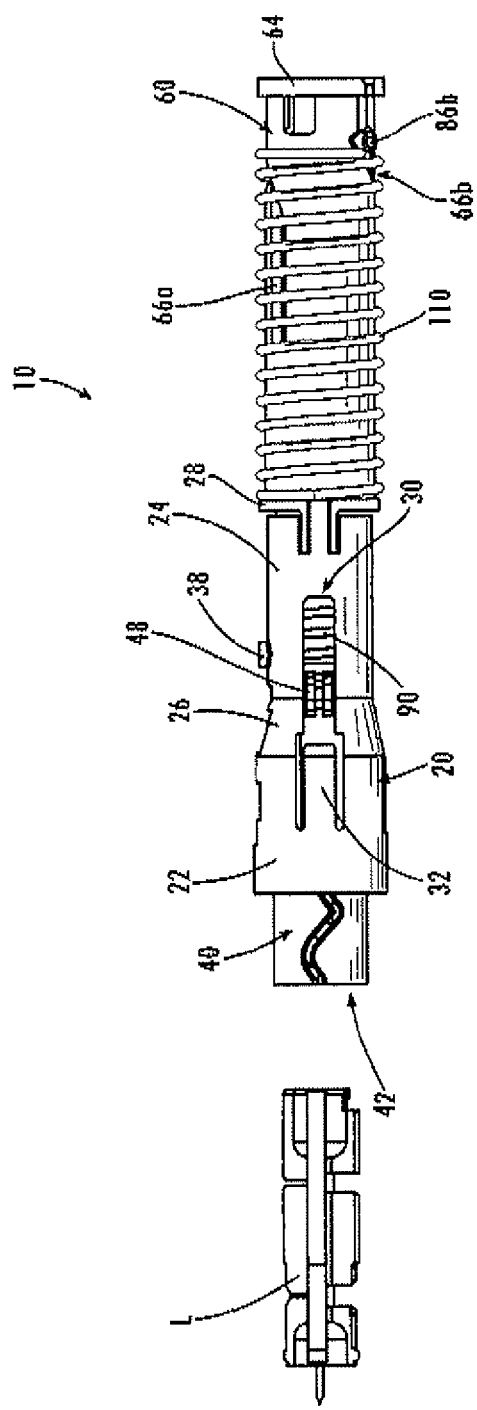
FIG. 2b is a side view of the mechanical drive core of FIG. 1, shown in the loading state.
Figure 3B:
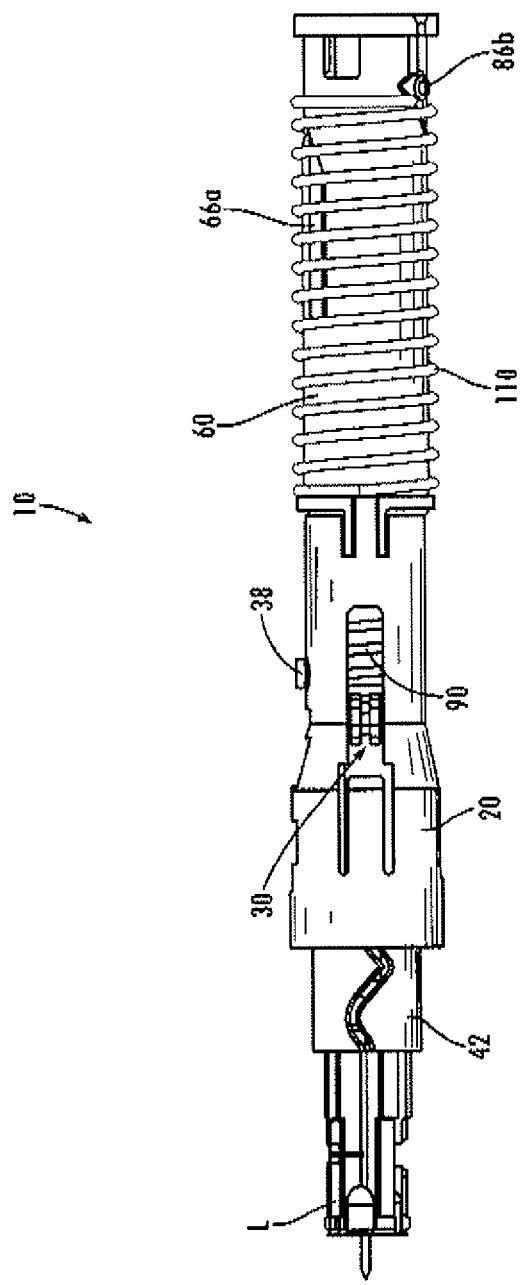
FIG. 3b is a side view of the mechanical drive core of FIG. 1, shown in the neutral state.

In use, a lancet L is loaded into the receiver 42 of the drive plunger 40, as shown in FIGS. 2 and 3. The depth-adjustment mechanism, if present, may be set to the desired lancing penetration depth, according to its specified manner of operation, for example as described above with reference to FIGS. 10 and 11.

Figure 4B:
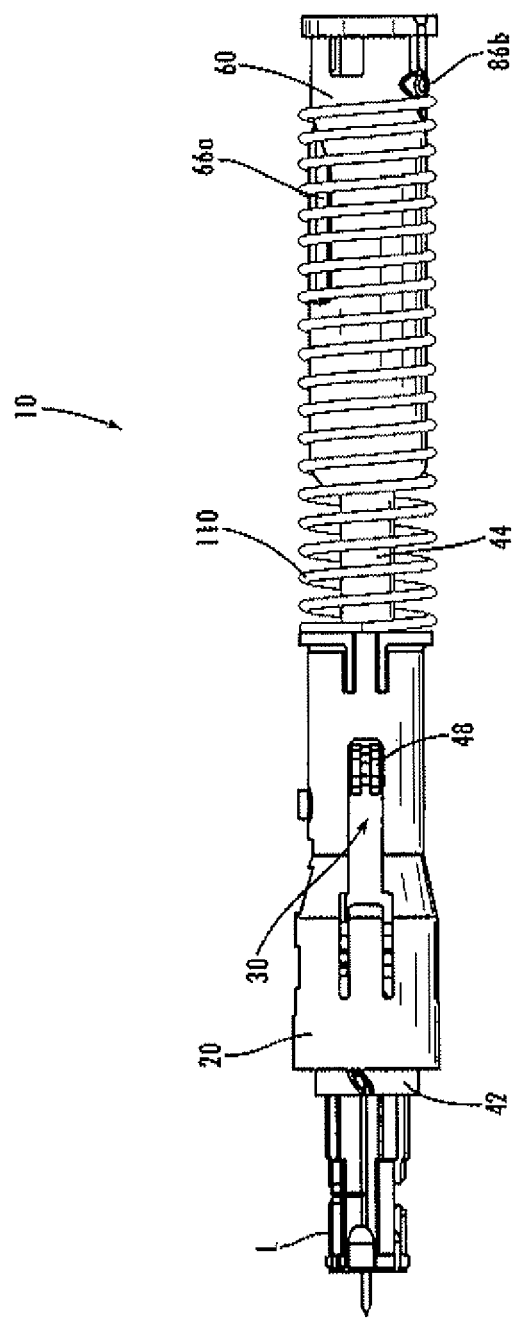
FIG. 4b is a side view of the mechanical drive core of FIG. 1, shown in the charging state.

Pulling the charging housing 60 distally away from the mechanism housing 20 compresses the return spring 100 between the expanded portion of the tail 46 of the drive plunger 40 and the rear face of flange 62 of the charging housing. As the return spring 100 reaches its fully compressed state, further retraction of the charging housing 60, as seen in FIG. 4, pulls the drive plunger 40 rearward within the mechanism housing 20, compressing and energizing the drive spring 90, until wing 48 of the drive plunger contacts the distal end of the slot 30 in the mechanism housing, and the free end of the trigger arm 50 clears the shoulder or catch member 35 of the trigger slot 32, in the retracted position of the drive plunger.

Figure 5A:
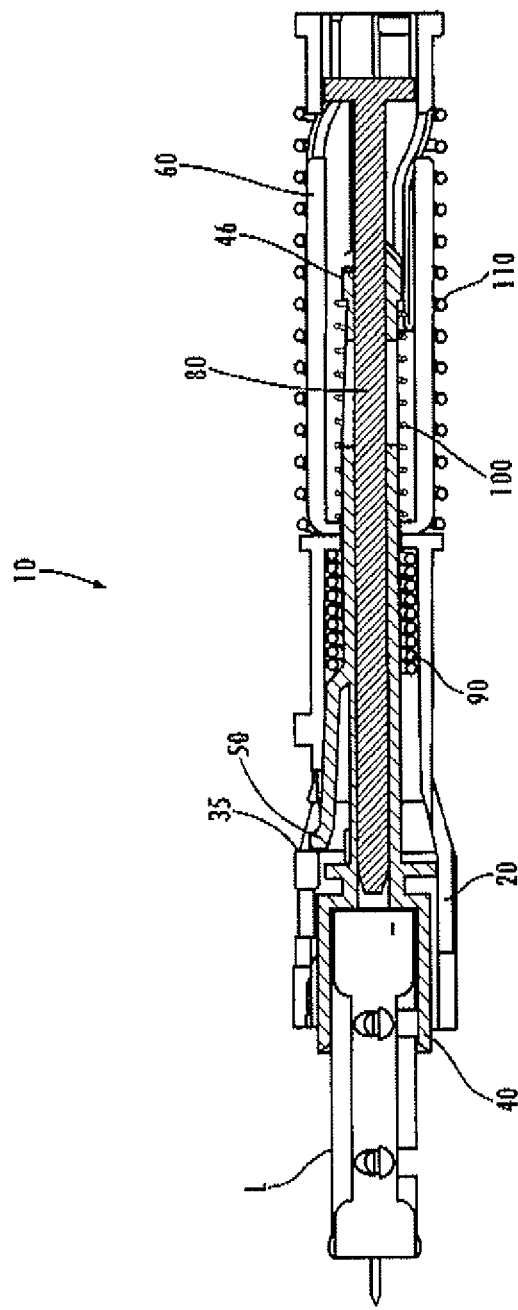
FIG. 5a is a cross-sectional side view of the mechanical drive core of FIG. 1, shown in a charged state.

Upon release of the charging housing 60, the return spring 100 extends to move the charging housing back against the mechanism housing 20. The drive plunger 40 is retained in its charged state by the engagement of the free end of the trigger arm 50 with the shoulder or catch member 35, resisting the bias of the compressed drive spring 90. FIG. 5 shows the independent drive core mechanism 10 in this charged or energized state. In this state, the rib 88 of the ejector rod is in alignment with the tail 46 of the retracted drive plunger 40, and the drive plunger thereby blocks forward advancement of the ejector rod to prevent inadvertent ejection of the lancet L from the receiver 42 of the drive plunger.

Figure 6A:
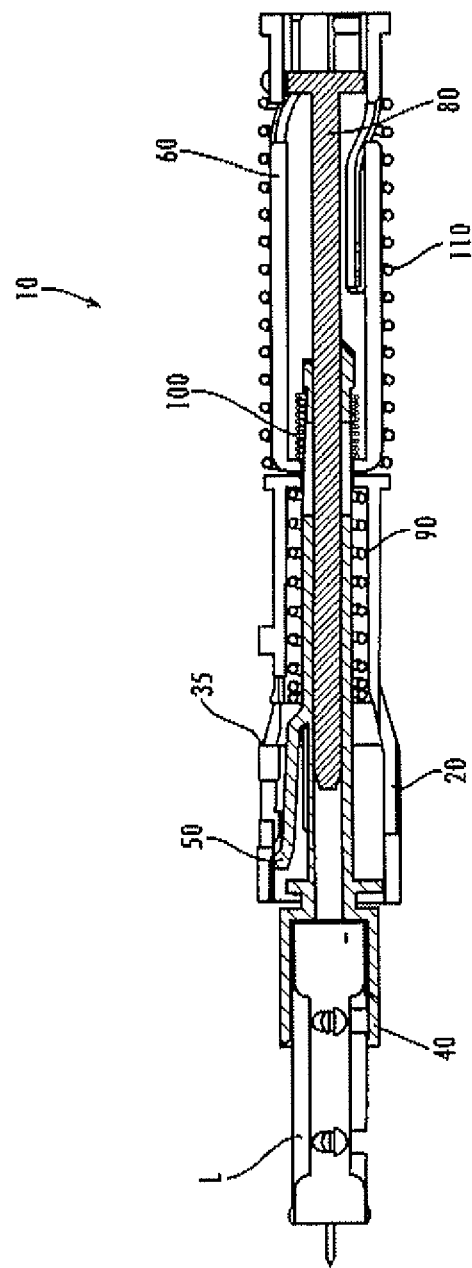
FIG. 6a is a cross-sectional side view of the mechanical drive core of FIG. 1, shown in an activated state.
Figure 6B:
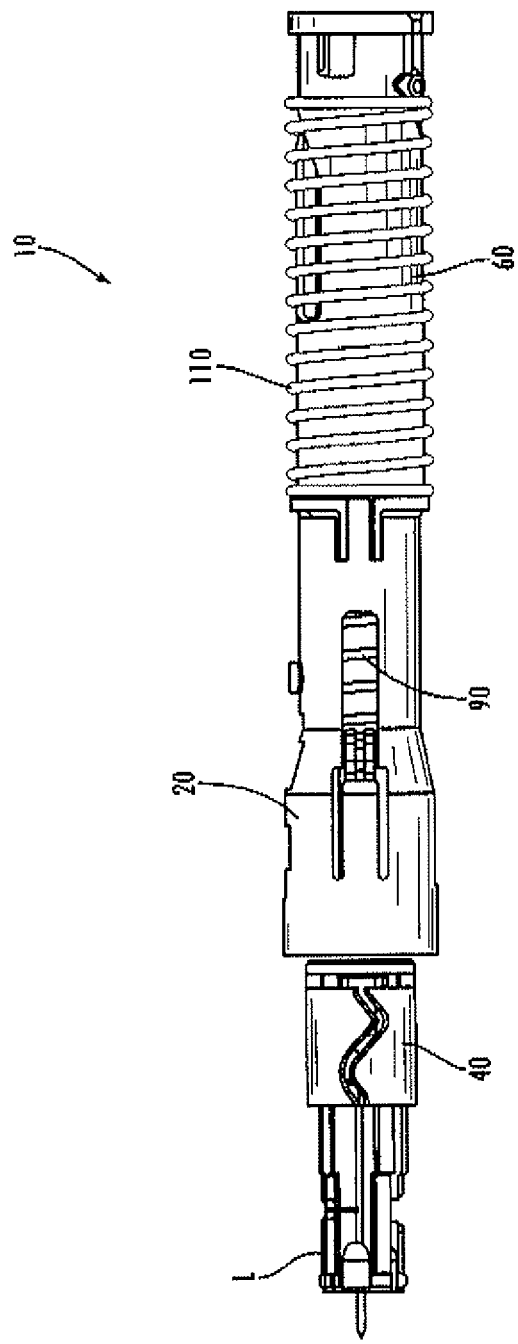
FIG. 6b is a side view of the mechanical drive core of FIG. 1, shown in the activated state.

The lancing device is then placed with its lancet opening 212, 212' against the desired lancing site of a human or animal subject. The release button 204, 204' is actuated to release the trigger arm 50 from engagement with the shoulder or catch member 35, allowing the drive spring 90 to propel the drive plunger 40 and the lancet L engaged therein forward or proximally, into its advanced position as shown in FIG. 6, wherein a sharp tip of the lancet projects a distance outwardly from the lancet opening to penetrate the subject's skin at the lancing site. The drive spring 90 is sufficiently stronger than the return spring 100 to propel the drive plunger through its lancing stroke. Contact of the wing 48 of the drive plunger against the proximal end of the slot 30 in the mechanism housing limits the forward travel of the drive plunger. After the lancing stroke is completed, the drive spring 90 and return spring 100 reach equilibrium at a neutral position of the drive plunger (FIGS. 2 and 7).

Figure 7A:
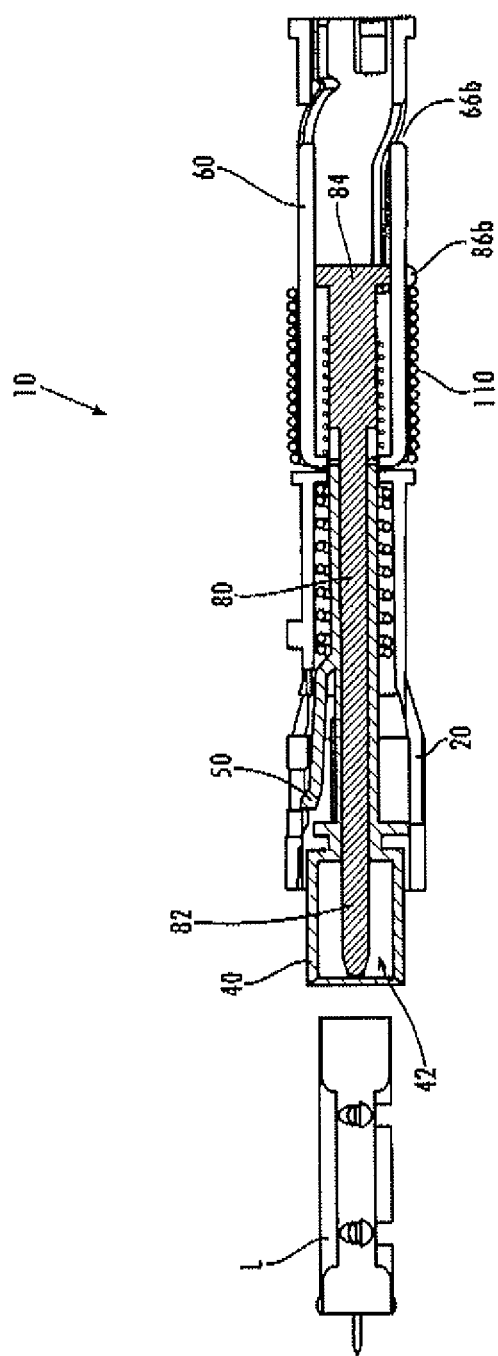
FIG. 7a is a cross-sectional side view of the mechanical drive core of FIG. 1, shown in an ejection state.
Figure 7B:
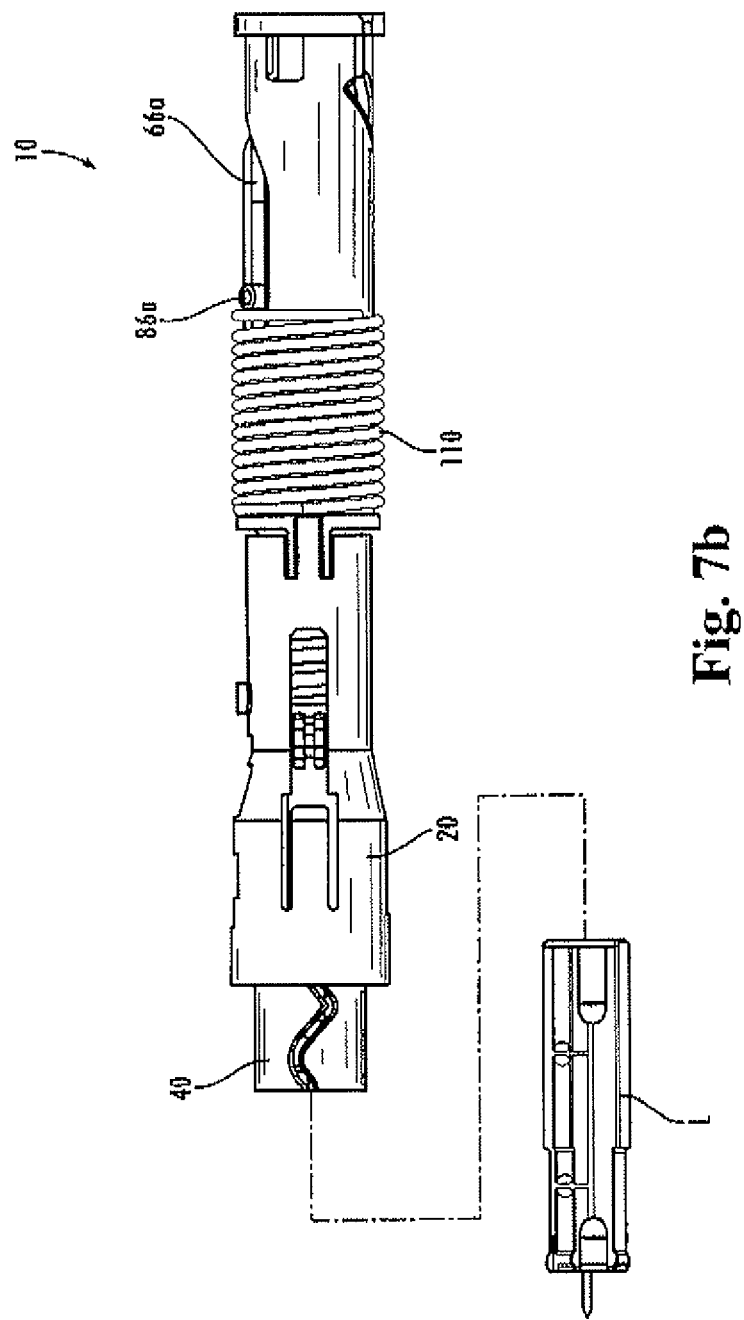
FIG. 7b is a side view of the mechanical drive core of FIG. 1, shown in the ejection state.
Figure 8A:
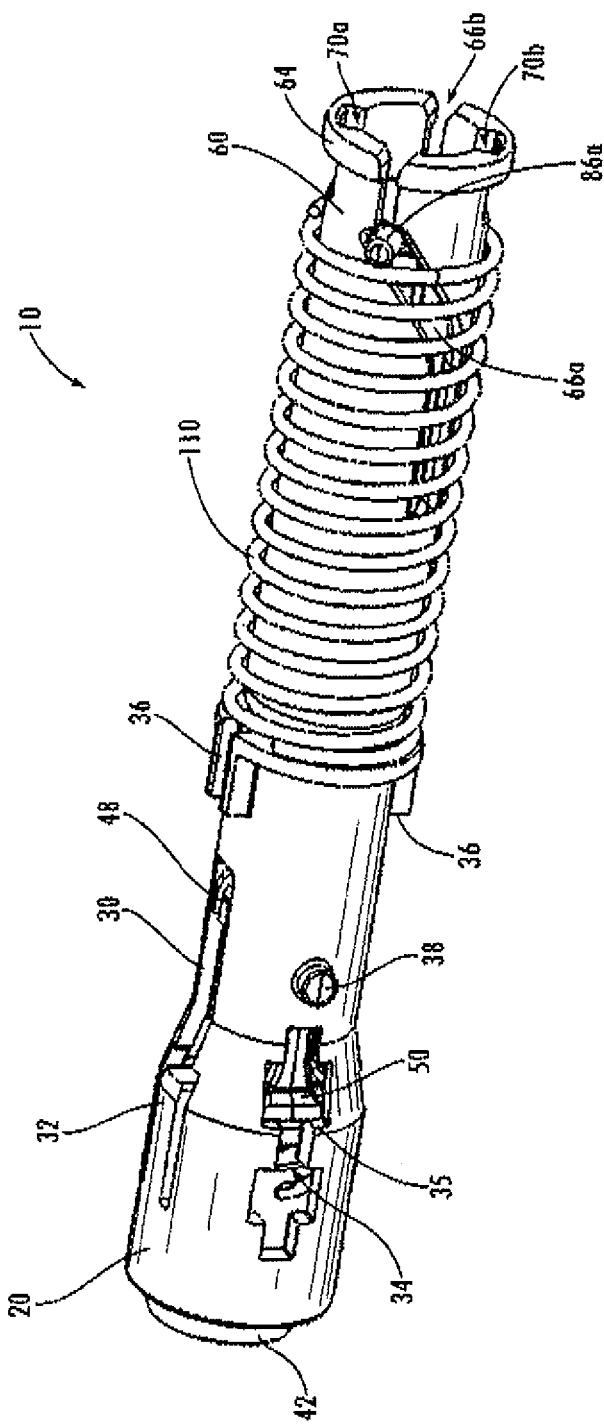
FIG. 8a is a perspective view of the mechanical drive core of FIG. 1, shown in a charged or pre-ejection state.
Figure 8B:
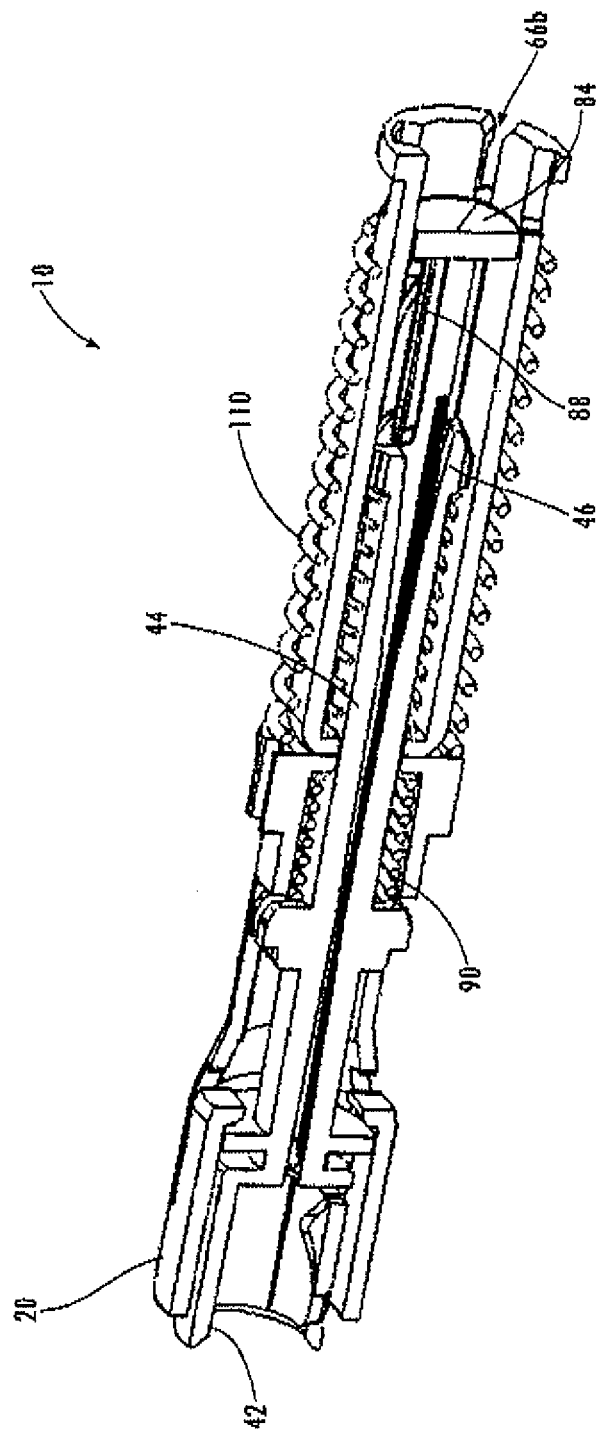
FIG. 8b is a cross-sectional perspective view of the mechanical drive core of FIG. 1, shown in a charged or pre-ejection state.
Figure 9A:
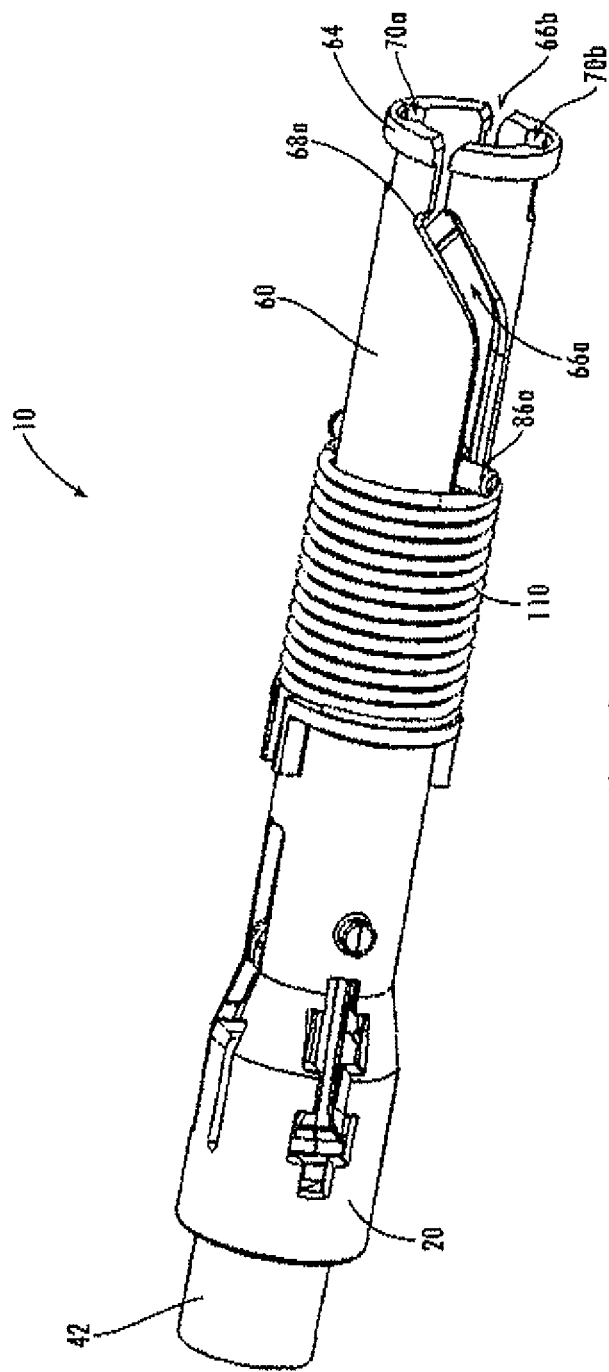
FIG. 9a is a perspective view of the mechanical drive core of FIG. 1, shown in the ejection state.
Figure 9B:
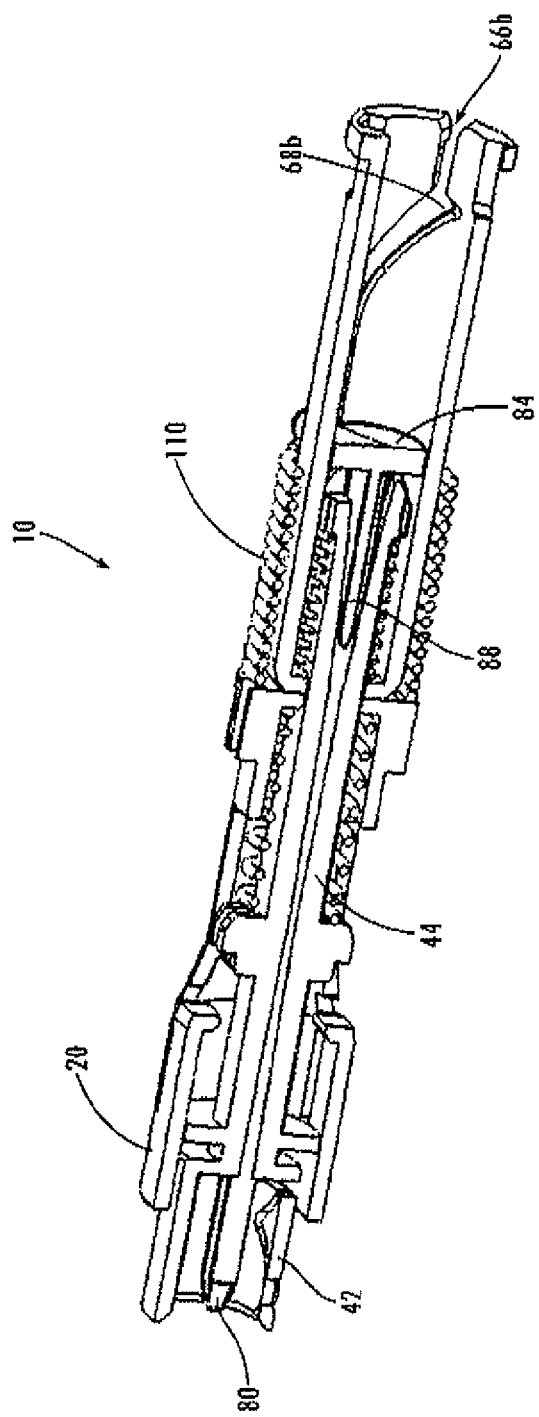
FIG. 9b is a cross-sectional perspective view of the mechanical drive core of FIG. 1, shown in the ejection state.

FIGS. 7-9 show the ejection sequence, whereby the used lancet L is ejected from the receiver 42 of the drive plunger 40 by actuation of the ejection actuator 208 of the lancing device. In the neutral state of the drive plunger 40, the ejector rod 80 may be advanced. As the pins 86a, 86b of the ejector rod 80 traverse the angled or arcuate medial portions of the slots 66a, 66b of the charging housing 60, the ejector rod twists, moving the rib 88 of the ejector rod out of alignment with the shelf or shoulder on the rear face of the tail 46 of the drive plunger 40, and into alignment with the slot of the drive plunger's tail. Comparing FIGS. 8 and 9, it can be seen that abutment of the rib 88 with the shoulder of the tail 46 blocks advancement of the ejector rod in the charged position (FIG. 8), whereas alignment of the rib 88 with the slot of the drive plunger's tail allows advancement of the ejector rod in the neutral position (FIG. 9). The cylindrical ejection rod 82 extends through the inner bore of the tube portion 44 of the drive plunger 40, through the tube's proximal end and into the receiver 42 (see FIG. 7), where it dislodges the lancet L from the receiver. The free end of the trigger arm 50 abuts a forward shoulder of the slot 34 in the ejection state (see FIG. 7a), to prevent the drive plunger from moving forward as the ejection rod presses against the back of the lancet. Advancing the ejection rod causes the pins 86a, 86b to compress the ejector spring 110 (see FIGS. 7 and 9), and upon release of the ejection actuator after lancet removal the ejector spring 110 expands to return the ejection rod to its retracted position. After removal, the used lancet is disposed of and the lancing device is ready for reuse.

Alternate Embodiments

While the invention has been described with reference to preferred and example embodiments, it will be understood by those skilled in the art that a variety of modifications, additions and deletions are within the scope of the invention, as defined by the following claims.

Figure 21A:
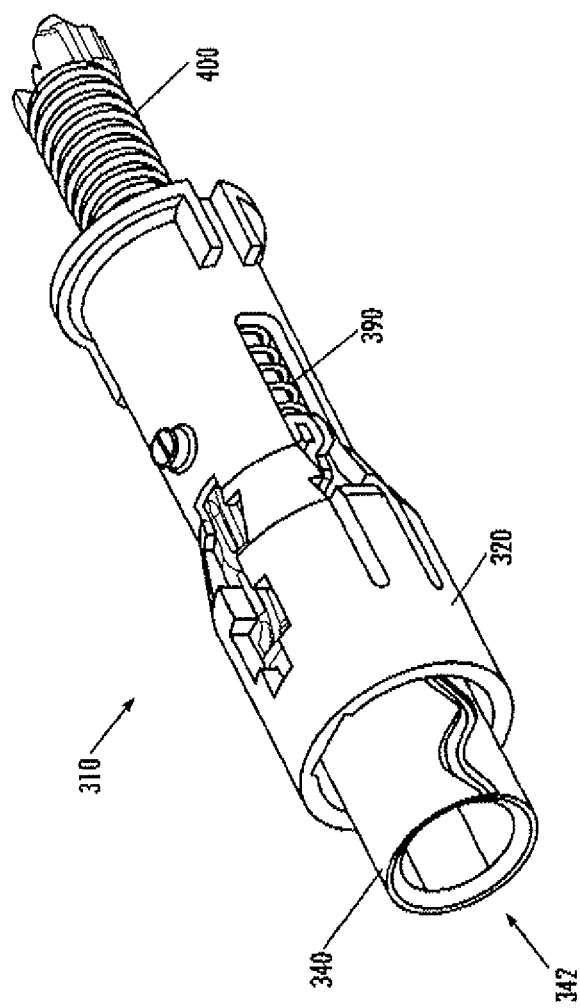
FIGS. 21a and 21B show perspective and cross-sectional views of a drive core mechanism according to another embodiment of the invention.
Figure 21B:
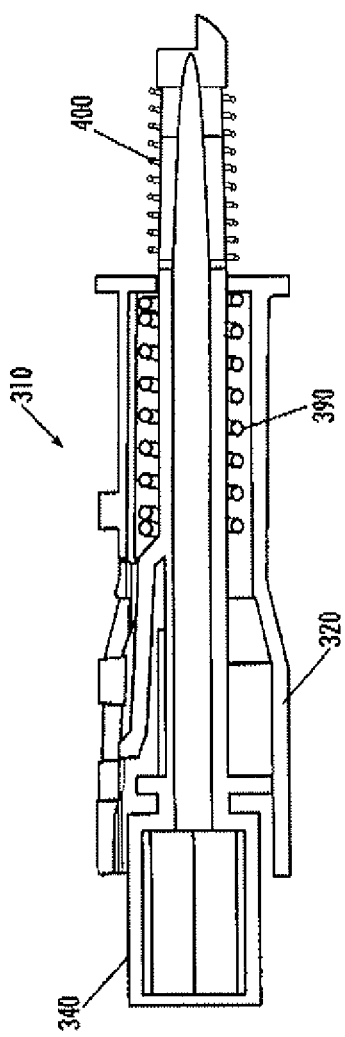
Figure 22:
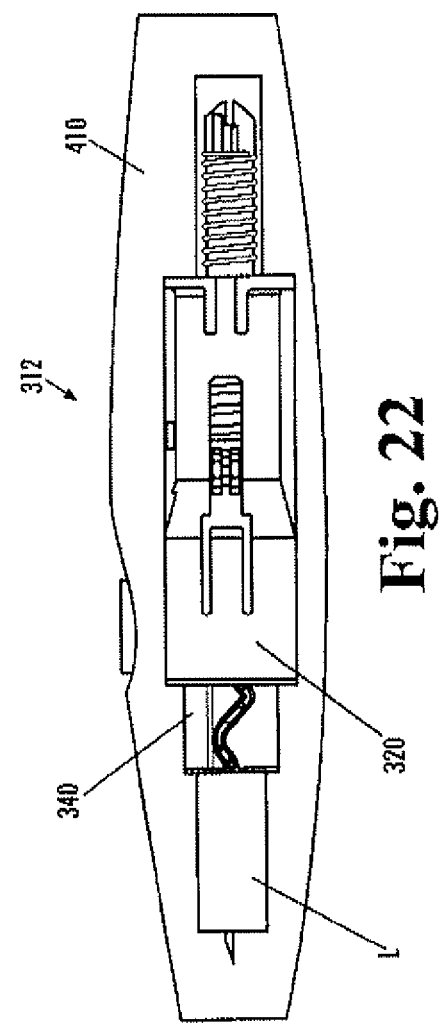
FIG. 22 shows a lancing device incorporating the drive core mechanism of FIG. 21 mounted in an external housing, according to another form of the invention.

For example, FIGS. 21 and 22 depict a drive core mechanism 310 and lancing device 312 according to an embodiment of the invention similar to that described above, but omitting the ejection and charging subassemblies. The drive core mechanism 310 includes a mechanism housing 320, a drive plunger 340, a drive spring 390, and a return spring 400, all substantially similar to corresponding components of the drive core mechanism 10 described above. Omission of the ejection and charging subassemblies results in a shorter overall mechanism, allowing use of a more compact outer housing 410. In this form of the invention, the user manually charges the drive mechanism by pushing the lancet L distally upon insertion, and manually removes the lancet by pulling it from the receiver 342 after use.

Figure 23:
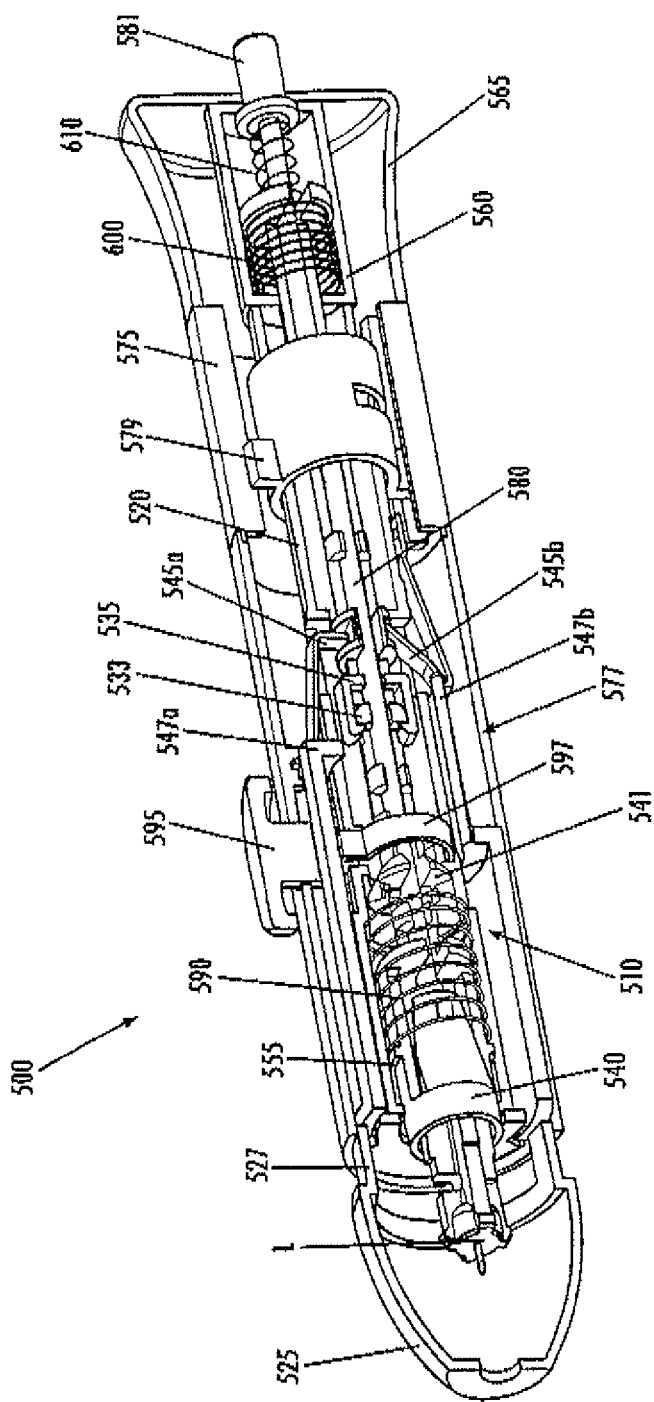
FIG. 23 shows a lancing device and drive core mechanism according to another embodiment of the invention.

FIG. 23 shows a lancing device 500 having an independent drive core mechanism or chassis 510 according to another embodiment of the invention. In this embodiment, the drive plunger 540 comprises a collet receiver having a plurality of flexing fingers that are opened by contact with the proximal end of the ejection rod 580 to release the lancet L during ejection upon pressing the ejection actuator 581. A stop 555 on the drive plunger contacts a cooperating flange or shoulder of the chassis housing 520 to limit the stroke of the drive plunger within the chassis. A rotationally mounted depth control ring portion 575 of the external housing 577 is coupled to a collar 579 having a helical slot engaging a pin or lug of the housing 520 to advance and retract the drive core mechanism 510 axially within the housing for lancing penetration depth adjustment. The release button 595 of the external housing includes an elongate fin for interfacing with a ring trigger 597 that deforms to selectively engage and release a flared catch portion 541 of the drive plunger 540. A coupling 533 may allow a degree of freedom along a short axial distance between the drive plunger 540 and the return plunger 535, to reduce transmission of vibration to the lancet for reduced pain, and/or to minimize the need for holding springs in compression during assembly. The drive spring 590 is located axially forward of the trigger release 595 to reduce vibration and lateral movement of the lancet during the lancing stroke. The return spring 600 and ejector spring 610 are positioned in the charging housing 560, which is coupled to a retractable charging actuator 565 of the external housing. A mechanism lock comprising a spring arm 545 (shown in alternate forms as 545a and 545b) engages the return plunger 535 to lock the drive core mechanism in position when the endcap 525 is removed from the external housing, to prevent inadvertent launching of a lancet, and for easier insertion and removal of the lancet. A flange 527 of the endcap interacts with a lock release 547 (shown in alternate forms as 547a and 547b) to release the spring arm 545 from the return plunger when the endcap is installed on the housing, allowing movement of the drive core mechanism.

What is claimed is:

1. A self-contained modular drive core for installation within a lancing device housing, the self-contained modular drive core comprising:
    an inner housing configured to be mounted at least partially within the lancing device housing, the inner housing having a channel extending therethrough;
    a drive plunger translationally mounted to move axially within the channel, the drive plunger movable relative to the inner housing along a lancing stroke between an advanced position and a retracted position;
    a drive mechanism for advancing the drive plunger, the drive mechanism coupled between the inner housing and the drive plunger;
    at least one retention feature on an external portion of the inner housing to engage a cooperating interface of the lancing device housing and movably couple the inner housing to the lancing device housing; and
    a depth-adjust interface operable between the inner housing and the lancing device housing, whereby adjustment of a depth control feature of the lancing device housing axially repositions the inner housing relative to the lancing device housing to adjust a lancing depth while maintaining a constant lancing stroke length of the drive plunger relative to the inner housing.

2. The self-contained modular drive core of claim 1, further comprising a charging housing for retracting the drive plunger and energizing the drive spring.

3. The self-contained modular drive core of claim 2, wherein the at least one retention feature comprises a channel in the charging housing.

4. The self-contained modular drive core of claim 1, wherein the lancing device housing includes one or more guidance surfaces for interfacing with cooperating portions of the drive core to restrict transverse movement and provide smooth axial movement of the independent drive core within the lancing device housing.

5. The self-contained modular drive core of claim 4, wherein the drive plunger further comprises a laterally projecting wing extending therefrom and sliding axially within a stroke-limiting slot formed in the inner housing when the drive plunger advances and retracts within the lancing device housing.

6. The self-contained modular drive core of claim 1, wherein the drive mechanism further comprises a drive spring for advancing the drive plunger in a first direction relative to the inner housing and a return spring opposing the drive spring for retracting the drive plunger in a second direction opposite the first direction.

7. The self-contained modular drive core of claim 1, further comprising an ejection member for releasing a lancet from the drive plunger.

8. The self-contained modular drive core of claim 1, wherein the depth control feature of the lancing device housing comprises a linearly actuated actuator to selectively control the axial position of the inner housing proximally or distally within lancing device housing.

9. The self-contained modular drive core of claim 8, further comprising multiple discrete indexed depth settings.

10. The self-contained modular drive core of claim 8, wherein the depth control feature of the lancing device housing further comprises a rotationally mounted depth-adjust collar coupled to the linearly actuated actuator.

11. The self-contained modular drive core of claim 1, wherein the depth-control feature on the lancing device housing comprises a rotationally actuated actuator to selectively control the axial position of the inner housing forward to back within lancing device housing.

12. The self-contained modular drive core of claim 11, wherein the rotationally actuated actuator comprises a depth-adjust collar having a slot that engages the retention feature of the inner housing of the drive core.

13. A lancing device comprising a lancing device housing and a self-contained modular drive core the self-contained modular drive core comprising:
   an inner housing mounted at least partially within the lancing device housing, the inner housing having a channel extending therethrough;
   a drive plunger translationally mounted to move axially within the channel, the drive plunger movable relative to the inner housing along a lancing stroke between an advanced position and a retracted position;
   a drive mechanism for advancing the drive plunger, the drive mechanism coupled between the inner housing and the drive plunger;
   at least one retention feature on an external portion of the inner housing to engage a cooperating interface of the lancing device housing and movably couple the inner housing to the lancing device housing; and
   a depth-adjust mechanism operable between the inner housing and the lancing device housing, whereby adjustment of a depth control feature of the lancing device housing axially repositions the inner housing relative to the lancing device housing to adjust a lancing depth while maintaining a constant lancing stroke length of the drive plunger relative to the inner housing.

* * * * *